US012102957B2

(12) United States Patent
Mbadinga Mouanda et al.

(10) Patent No.: US 12,102,957 B2
(45) Date of Patent: Oct. 1, 2024

(54) DEVICE FOR THE COMBINED REDUCTION OF THE CARBON DIOXIDE AND WATER OR MOISTURE CONTENT, MOTOR VEHICLE, AND METHOD

(71) Applicant: MANN+HUMMEL GmbH, Ludwigsburg (DE)

(72) Inventors: Gelase Mbadinga Mouanda, Sachsenheim (DE); Thomas Jessberger, Asperg (DE); Achim Janner, Ludwigsburg (DE)

(73) Assignee: MANN+HUMMEL GmbH, Ludwigsburg (DE)

( * ) Notice: Subject to any disclaimer, the term of this patent is extended or adjusted under 35 U.S.C. 154(b) by 429 days.

(21) Appl. No.: 17/488,804

(22) Filed: Sep. 29, 2021

(65) Prior Publication Data
US 2022/0016567 A1  Jan. 20, 2022

Related U.S. Application Data

(63) Continuation of application No. PCT/EP2020/058334, filed on Mar. 25, 2020.

(30) Foreign Application Priority Data

Mar. 29, 2019 (DE) .................... 10 2019 108 348.6

(51) Int. Cl.
*B01D 53/04* (2006.01)
*A61L 9/16* (2006.01)
(Continued)

(52) U.S. Cl.
CPC ............ *B01D 53/0446* (2013.01); *A61L 9/16* (2013.01); *B01D 53/0438* (2013.01);
(Continued)

(58) Field of Classification Search
None
See application file for complete search history.

(56) References Cited

U.S. PATENT DOCUMENTS

| 6,599,347 B2 | 7/2003 | Kalbassi et al. |
| 7,601,189 B2 | 10/2009 | Lampinen et al. |

(Continued)

FOREIGN PATENT DOCUMENTS

| CN | 201432564 Y | 3/2010 |
| DE | 4304075 A1 | 8/1994 |

(Continued)

OTHER PUBLICATIONS

JP2015174463A_ENG (Espacenet machine translation of Hirano) (Year: 2015).*

*Primary Examiner* — Gabriel E Gitman

(57) ABSTRACT

A device for reducing a carbon dioxide and water content in an enclosed air volume has first and second sorption units for sorbing carbon dioxide and water. The first and second sorption units can be transferred from a sorption mode into a desorption mode and vice versa. In the sorption mode, the first and second sorption units sorb carbon dioxide and water from raw air of the enclosed air volume. In the desorption mode, the first and second desorption units desorb carbon dioxide and water to supplied regeneration air. An air distribution device can switch the first and second sorption units, based on the carbon dioxide and water content, alternately from sorption mode into desorption mode such that, in at least one operating state of the device, one of the first and second sorption units is in sorption mode while the other is in desorption mode.

24 Claims, 21 Drawing Sheets

(51) Int. Cl.
*B01D 53/26* (2006.01)
*B60H 3/02* (2006.01)
*B60H 3/06* (2006.01)

(52) U.S. Cl.
CPC ....... *B01D 53/0454* (2013.01); *B01D 53/261* (2013.01); *B60H 3/024* (2013.01); *B60H 3/0633* (2013.01); *A61L 2209/22* (2013.01); *B01D 2257/404* (2013.01); *B01D 2257/504* (2013.01); *B01D 2257/708* (2013.01); *B01D 2257/80* (2013.01); *B01D 2257/91* (2013.01); *B01D 2259/4009* (2013.01); *B01D 2259/40096* (2013.01); *B01D 2259/402* (2013.01); *B01D 2259/4566* (2013.01); *B60H 2003/028* (2013.01); *B60H 2003/0691* (2013.01)

(56) References Cited

U.S. PATENT DOCUMENTS

| | | | |
|---|---|---|---|
| 8,840,704 B2 | 9/2014 | Shoji et al. | |
| 9,388,994 B2 | 7/2016 | Hidaka et al. | |
| 9,975,087 B2 | 5/2018 | Eisenberger | |
| 10,046,266 B2 | 8/2018 | Meirav et al. | |
| 10,507,424 B1 | 12/2019 | Muller-Hellwig et al. | |
| 10,507,927 B2 * | 12/2019 | Ludvik | B01D 53/0462 |
| 10,646,815 B2 | 5/2020 | Luisman et al. | |
| 10,765,990 B2 | 9/2020 | Meirav et al. | |
| 10,913,026 B2 | 2/2021 | Meirav et al. | |
| 11,369,914 B2 | 6/2022 | Smith et al. | |
| 2002/0056373 A1 | 5/2002 | Fielding | |
| 2005/0217487 A1 * | 10/2005 | Fielding | B60H 3/0633 96/121 |
| 2011/0265648 A1 | 11/2011 | Meirav | |
| 2013/0283842 A1 | 10/2013 | Heyse et al. | |
| 2014/0053729 A1 * | 2/2014 | Crooks | B01D 53/002 95/139 |
| 2014/0165515 A1 * | 6/2014 | Matsuda | D04H 3/016 55/482 |
| 2016/0074803 A1 * | 3/2016 | Gebald | B01D 53/0446 95/139 |
| 2016/0103111 A1 * | 4/2016 | Griffin | B60N 2/002 73/25.01 |
| 2016/0288043 A1 | 10/2016 | Meirav et al. | |
| 2017/0239609 A1 * | 8/2017 | Luisman | B01J 20/3242 |
| 2019/0092143 A1 | 3/2019 | Kakizaki et al. | |
| 2019/0160418 A1 * | 5/2019 | Matsumoto | B01D 53/261 |

FOREIGN PATENT DOCUMENTS

| | | | | |
|---|---|---|---|---|
| DE | 19512844 A1 | 10/1996 | | |
| DE | 19527638 A1 | 1/1997 | | |
| DE | 19734440 C1 | 9/1998 | | |
| DE | 102014007735 A1 | 12/2014 | | |
| DE | 102017208228 A1 | 11/2018 | | |
| DE | 112017001495 T5 | 12/2018 | | |
| EP | 2716987 A2 | 4/2014 | | |
| FR | 3055585 A1 | 3/2018 | | |
| FR | 3062604 A1 | 8/2018 | | |
| GB | 1221549 A | 2/1971 | | |
| GB | 2521450 A | 6/2015 | | |
| GB | 2548621 A | * | 9/2017 | ......... B01D 53/0407 |
| JP | H05137958 A | 6/1993 | | |
| JP | 2015174463 A | * | 10/2015 | |
| WO | 2009092552 A1 | 7/2009 | | |
| WO | 2010100739 A1 | 9/2010 | | |
| WO | 18029352 A1 | 2/2018 | | |

* cited by examiner

DEVICE FOR THE COMBINED REDUCTION OF THE CARBON DIOXIDE AND WATER OR MOISTURE CONTENT, MOTOR VEHICLE, AND METHOD

CROSS-REFERENCE TO RELATED APPLICATIONS

This application is a continuation application of international application No. PCT/EP2020/058334 having an international filing date of 25 Mar. 2020 and designating the United States, the international application claiming a priority date of 29 Mar. 2019 based on prior filed German patent application No. 10 2019 108 348.6, the entire contents of the aforesaid international application and the aforesaid German patent application being incorporated herein by reference.

TECHNICAL FIELD

The present invention concerns a device for the combined reduction of the carbon dioxide and water or moisture content in an enclosed air volume, in particular in a passenger compartment of a motor vehicle; a motor vehicle with such a device; and a method for operating such a device.

BACKGROUND OF THE INVENTION

In at least partially electrically driven motor vehicles, for reaching a range as large as possible it is productive to save as much energy as possible. Usually, for reasons of comfort a passenger compartment of such a motor vehicle can be air conditioned by means of an air conditioning device. With regard to the desired energy savings, it is advantageous when the air conditioning device for air conditioning the passenger compartment takes in and heats or cools as little fresh air as possible from the environment of the motor vehicle but instead recirculates and air conditions the air contained in the passenger compartment in recirculating operation.

In the aforementioned recirculating operation for air conditioning the passenger compartment, the water contained in the exhalation air of the passengers can however accumulate in the passenger compartment which leads to fogging of window panes, for example, of a windshield or side windows of the motor vehicles. The reason for this is that the moisture-removing effect of an air conditioning device, which results from a drop below the dew point in the evaporator heat exchanger, cannot be used in recirculating operation. This is to be avoided or at least to be reduced with respect to safety aspects.

Moreover, carbon dioxide contained in the exhalation air may also accumulate in the passenger compartment. This can lead to loss of concentration or even health impairment of the occupant. This also has to be prevented or at least to be reduced with respect to safety aspects as well as with respect to health aspects because in the worst case, due to a carbon dioxide concentration that is too high in the passenger compartment air, the power of concentration of the driver can be reduced so greatly that accidents are imminent.

SUMMARY OF THE INVENTION

It is therefore object of the invention to provide an improved device for reduction of the carbon dioxide and water content for a passenger compartment of a motor vehicle.

Accordingly, a device for combined reduction of the carbon dioxide and water content in an enclosed air volume, in particular in a passenger compartment of a motor vehicle, is proposed. The device comprises a first sorption unit for combined sorption of carbon dioxide and water, a second sorption unit for combined sorption of carbon dioxide and water, wherein the first sorption unit and the second sorption unit each contain a plurality of sorbents, wherein the sorption units each can be transferred from a sorption mode, in which the sorption units sorb carbon dioxide and water from raw air of the enclosed air volume, into a desorption mode, in which the sorption units desorb carbon dioxide and water to supplied regeneration air, and vice versa, and an air distribution unit by means of which, as a function of the carbon dioxide and water content in the enclosed air volume, the sorption units each can be switched alternately from the sorption mode into the desorption mode and vice versa such that, in at least one operating state of the device, one of the two sorption units is in the sorption mode while the other of the two sorption units is in the desorption mode.

According to a preferred embodiment, it can be provided that, in the desorption mode, the regeneration air that is guided through the sorption unit which is in the desorption mode can be supplied as loaded regeneration air to an environment, in particular via a desorption conduit.

The motor vehicle is preferably an electric vehicle or a hybrid vehicle. However, the motor vehicle can also be driven by means of an internal combustion engine or of a combustion motor. The motor vehicle comprises in particular a car body that encloses the enclosed air volume. In this context, "enclosed" means that the car body defines the boundaries or a geometric expansion of the air volume. This means in particular but not mandatorily that the enclosed air volume cannot be in air exchange with an environment of the motor vehicle. The enclosed air volume is preferably the passenger compartment of the motor vehicle.

In particular occupants or passengers are staying in the enclosed air volume. The enclosed air volume is not mandatorily associated with a motor vehicle. The enclosed air volume can also be associated with a watercraft, a construction machine or a construction vehicle, a rail vehicle, an agricultural machine or an agricultural vehicle, or an aircraft. The enclosed air volume however can also be part of a building or of a stationary machine.

In particular, the device or the air distribution device is controlled on the basis of sensor signals. For this purpose, a control unit can be provided. Moreover, preferably sensors, in particular pressure sensors, temperature sensors and/or sensors for detecting the carbon dioxide and water content are provided. For example, the sorption mode is activated when the carbon dioxide content rises above a certain value.

The sorption units are suitable in particular to adsorb carbon dioxide and water. The sorption units can also be suitable to absorb carbon dioxide and water. "Sorption" is to be understood presently as processes which lead to accumulation of a substance, for example, of carbon dioxide or water, inside a phase or at a boundary surface between two phases. The accumulation within a phase is referred to as absorption, the accumulation at the boundary surface is referred to as adsorption. "Desorption" is understood presently as processes in which atoms or molecules, in particular carbon dioxide or water, leave the surface of a solid body. The desorption thus represents generally the reversal of sorption.

The sorption units can be pure adsorption units or can be referred to as such. Preferably, the sorption units each comprise a cartridge form so that they can be easily and quickly exchanged. The sorption units can comprise a cylindrical, in particular a hollow cylindrical, a plate-shaped, a pie-shaped or any other geometry.

The sorption units each comprise preferably a plurality of sorbents or sorption agents. In particular, a sorbent can be provided that is suitable to sorb, preferably to adsorb, carbon dioxide. This sorbent can be referred to as carbon dioxide sorbent or $CO_2$ sorbent. A further sorbent can be provided that is suitable to sorb, in particular to adsorb, water. This sorbent can be referred to as water sorbent or $H_2O$ sorbent. The sorbents can be present in granular form or fiber form, in particular in the form of a bulk material. In particular, the sorbents are fixed by means of a carrier material. The sorbents can also be pure adsorbents or can be referred to as such.

The sorption mode can also be a pure adsorption mode or can be referred to as such. The desorption mode can also be referred to as regeneration mode. That the sorption units each are "transferable" from the sorption mode into the desorption mode and vice versa is to be understood in particular such that switching can be performed back and forth between the sorption mode and the desorption mode. This switching is realized preferably by means of the air distribution device in such a way that the sorption units are supplied either with the raw air or the regeneration air. For this purpose, the air distribution device preferably comprises a plurality of valves or flaps. The air distribution device can be a flap system or a flap device or can be referred to as such.

That the air distribution device is suitable to "alternately" switch the sorption units is to be understood in particular such that, for example, the first sorption unit is in the sorption mode while the second sorption unit is in the desorption mode. After switching by means of the air distribution device, this is exactly reversed.

The regeneration air can be taken from the enclosed air volume or the environment of the motor vehicle. Initially, the regeneration air is not loaded. In the desorption mode, the non-loaded regeneration air is loaded with carbon dioxide and water and is supplied as loaded regeneration air to the environment. That the regeneration air is not loaded with carbon dioxide and water is to be understood in particular such that the regeneration air can take up carbon dioxide and water that is stored in the sorption unit which is in the desorption mode. However, this does not preclude that the non-loaded regeneration air may also contain a certain quantity of carbon dioxide and water. However, the non-loaded regeneration air is not saturated with carbon dioxide and water. Therefore, the non-loaded regeneration air can also be taken from the enclosed volume.

Since the sorption units are operated alternately, an interruption-free and thus continuous reduction of the carbon dioxide and water content in the enclosed air volume is possible. This means that in the enclosed air volume a recirculation operation can take place without having to take in ambient air from the environment in order to keep the carbon dioxide and the water content sufficiently low. Thus, the accumulation of carbon dioxide and water in the enclosed air volume with the disadvantages explained in the introduction can be prevented reliably. By dispensing with the supply of ambient air into the vehicle air conditioning system, an energy savings can be achieved because cooling or heating of supplied ambient air can be dispensed with. In case that the motor vehicle is operated electrically, this leads to an extension of the range of the motor vehicle. Moreover, by dispensing with supply of ambient air, the service life of an interior filter of the motor vehicle can also be extended because no particulate matter must be filtered out from the ambient air. A further advantageous effect results in that the components of a vehicle air conditioning system (respective heat exchangers for heat sink and heat source, compressor etc.) can be designed smaller which provides potential for downsizing.

In embodiments, the air distribution device comprises a plurality of valves which can be switched such that, in operation of the device, the raw air from the enclosed air volume can be supplied to the sorption unit which is in the sorption mode in order to remove the carbon dioxide and the water from the raw air and the regeneration air can be supplied to the sorption unit which is in the desorption mode in order to remove the carbon dioxide and the water from the sorption unit. Preferably, four valves are provided. The valves can be flap valves. Preferably, the valves are multi-way valves, in particular three-way valves or 4-, 6-, 8-way valves.

In embodiments, the device comprises moreover at least one heating element for introducing heat into the sorption unit which is in the desorption mode. Preferably, each sorption unit has correlated therewith such a heating element. The heating element can be a heating wire that extends through the respective sorption unit. The heat can however also be introduced in any other way into the sorption unit which is in the desorption mode. For example, the heat can be waste heat of an electric motor for driving the motor vehicle. The heater is expediently only switched on when the respective sorption unit is in the desorption mode.

In embodiments, each sorption unit has integrated therein a heating element. This means that the heating element is connected fixedly to its associated sorption unit, in particular non-separably. This can be realized, for example, by means of a heating wire that has been mentioned before. In particular, the first sorption unit has associated therewith a first heating element and the second sorption unit has associated therewith a second heating element. Each sorption unit can comprise a plurality of heating elements.

In embodiments, the heating element is positioned upstream of the sorption unit. "Upstream" means presently in front of the sorption units along a flow direction of the non-loaded regeneration air supplied to the sorption units. The heating element in this case is not integrated in the sorption units. The heating element is in particular arranged outside of the sorption units. The heating element introduces heat into the non-loaded regeneration air which, in the desorption mode of the respective sorption unit, takes up water and carbon dioxide and is guided away from the sorption units as loaded regeneration air. The heating element can be a heat exchanger or comprise a heat exchanger. The heat which is employed for heating can be taken from a cooling agent circuit, for example, of a conventional internal combustion engine, a battery cooling system or a fuel-cell cooling circuit. In addition, the sorption units can however also comprise heating elements integrated therein.

In embodiments, the sorption units comprise a common heating element. This means that for both sorption units only one or precisely one heating element is provided. In this way, a separate heating element for each sorption unit can be dispensed with.

In embodiments, the device comprises moreover a regeneration valve which comprises a first switch position in which the regeneration air can be supplied from an environment of the enclosed air volume to the sorption unit which is in the desorption mode; a second switch position in which the regeneration air can be supplied from the enclosed air volume to the sorption unit which is in the desorption mode; and in particular a third switch position in which the sorption unit which is in the desorption mode can be regenerated under vacuum. The regeneration valve is preferably a three-way valve. Downstream of the regeneration valve, a check valve can be provided that prevents return flow of the regeneration air loaded with carbon dioxide and water into the enclosed air volume.

In embodiments, the device comprises moreover a blower device which supplies the raw air to the sorption unit which is in the sorption mode. The blower device is preferably a fan. The blower device can also be referred to as first blower device or as a sorption blower device. A sorption performance of the sorption unit which is in the sorption mode can be adapted, for example, by a change of a volume flow which is generated by the blower device. The volume flow can be influenced by means of a rotary speed change of the blower device.

In embodiments, the blower device is part of an air conditioning device. In this way, it is possible to save an own blower device for the device. In particular, the device can be partially or completely integrated into the air conditioning device. Alternatively, the device, as a modular component, can also be completely separate from the air conditioning device and thus be self-sufficient.

In embodiments, the device comprises moreover a blower device which supplies the regeneration air to the sorption unit which is in the desorption mode, wherein the blower device, in relation to the sorption units, is arranged at the pressure side or at the suction side. The blower device is preferably a fan. The blower device can also be referred to as second blower device or as desorption blower device. The first blower device and the second blower device can comprise a common drive element that, by means of couplings, can be coupled to blower wheels of the blower devices and decoupled therefrom. In this way, a drive element can be saved. The drive element is in particular an electric motor.

In embodiments, the device can moreover comprise a bypass conduit and a bypass valve that selectively can be switched from a first switch state, in which the raw air can be supplied to the desorption unit which is in the sorption mode, into a second switch state, in which the raw air by means of the bypass conduit can be guided by bypassing the sorption units back into the enclosed air volume, and vice versa. The second switch state (bypass) is selected preferably when the carbon dioxide and water content is below a predetermined value and thus no reduction of the carbon dioxide and water content in the enclosed air volume is required. Alternatively, the bypass conduit can also be actively switched in order to perform sensor tests or calibrations and/or when the pressure loss across one of the sorption units surpasses a predetermined limit value.

According to a further embodiment, a second bypass conduit as well as a second bypass valve can be provided. The second bypass valve can be switched from a first switch state, in which the regeneration air is supplied to the sorption unit which is in the desorption mode, into a second switch state, in which the regeneration air can be guided by means of the bypassing conduit so as to bypass the sorption units into the environment, and vice versa. The second switch state which is a desorption bypass is advantageously used in order to test sensors optionally provided in the system or when the pressure loss across one of the sorption units surpasses a predetermined limit value.

Yet another embodiment variant provides to provide, downstream at the pressure side of the desorption blower device, a branch in the desorption conduit which can be switched by means of a recirculation valve. The branch opens into a recirculation conduit which is connected in fluid communication with an inlet of the regeneration valve or opens downstream of an outlet of the regeneration valve into a regeneration air conduit that is connected to the outlet.

In this way, it is achieved that at least a portion of the volume flow which is conveyed by the desorption blower device is recirculated, i.e., can be guided multiple times across the sorption unit which is currently in the desorption mode.

This has primarily energetic advantages because the heat quantity introduced for regeneration is not guided into the environment after a single pass through the sorption unit which is in the desorption mode but is recirculated (guided in a circuit) until the air with regard to CO2 and/or water quantity is completely loaded, i.e., saturated. In this way, as a result the energy consumption of the heating device can be drastically reduced which further positively influences an energy-efficient operation of the whole device.

According to an embodiment, the branch can be switched by means of a recirculation valve so that by means of the desorption blower device the regeneration air can be selectively recirculated through the sorption units or can be guided into the environment.

With regard to the return into the regeneration air conduit, there are now various possibilities.

First, according to an embodiment, the recirculation conduit can be connected in fluid communication with an inlet of the regeneration valve wherein, by means of the regeneration valve, a fourth switch position can be switched in which the regeneration air can be supplied from the recirculation conduit to the sorption unit which is in the desorption mode, and vice versa.

According to this embodiment, no continuous supply of non-loaded regeneration air from the environment takes place but instead it is provided to switch the regeneration valve as well as the recirculation valve in pairs in a cyclic fashion in order to enable a supply of non-loaded fresh air and discharge of loaded regeneration air from the "recirculation circuit".

According to a second embodiment, which is preferred, it can be provided that a throttle valve, in particular an adjustable throttle valve, is arranged in relation to fluid communication between the outlet of the regeneration valve and the inlet of the recirculation conduit into the regeneration air conduit.

According to this embodiment, now a continuous supply of non-loaded regeneration air from the environment can be realized wherein the rate at which the non-loaded regeneration air from the environment is supplied to the "recirculation circuit" can be adjusted as needed.

In embodiments, the sorption units are suitable to remove, aside form carbon dioxide and water, also fine particles, nitrogen oxides and/or volatile organic compounds from the raw air. For this purpose, further suitable sorbents can be provided. Moreover, the sorption units may comprise a suitable filter medium for filtering the fine particles. The filter medium can function as a carrier material for the sorbents.

In embodiments, the sorption units comprise a first sorbent that is suitable to adsorb carbon dioxide, a second sorbent that is suitable to adsorb water, and further sorbents that are suitable to remove fine particles, nitrogen oxides and/or volatile organic compounds from the raw air, wherein the further sorbents are introduced between two carrier layers, in particular of a nonwoven, or wherein the sorbents and the further sorbents are mixed with each other. The number and type of the further sorbents is arbitrary. The further sorbents can comprise active carbon which, in particular in the form of a bulk material, is introduced preferably between the two carrier layers. The additional sorbent or the additional sorbents can be mixed with the CO2 sorbent and/or the H2O sorbent in order to build one or a plurality of mixed bulk materials.

In embodiments, the sorption units are suitable to remove, aside from carbon dioxide and water, also allergens, bacteria and/or viruses from the raw air. This can be realized by a functional coating of carrier materials, for example, of nonwovens, or by a functional coating of the sorbents. Moreover, the sorption units can comprise at least one scent component in regard to a comfort aspect.

Moreover, a motor vehicle with such a device is proposed. In this context, the device can be controlled on the basis of an occupation state of the enclosed air volume with passengers in order to keep the carbon dioxide and water content in the enclosed air volume in a predetermined tolerance field, independent of the occupation state. In this way, it is always ensured that the carbon dioxide and water contents does not rise undesirably. By adjustment to the occupation state, energy can be saved because, for example, for an occupation state with one passenger, a reduced conveying performance of the first blower device can be selected in comparison to an occupation state with four passengers. The occupation state can be detected, for example, by means of weight sensors or optical sensors.

Furthermore, a method for operating such a device for combined reduction of the carbon dioxide and water content in an enclosed air volume, in particular in a passenger compartment of a motor vehicle, is proposed. In this context, the device comprises a first sorption unit for combined sorption of carbon dioxide and water, a second sorption unit for combined sorption of carbon dioxide and water, and an air distribution device for alternately switching of the sorption units from sorption mode into a desorption mode and vice versa. The method comprises the following steps: a) switching of one of the two sorption units as a function of the carbon dioxide and water content in the enclosed air volume by means of the air distribution device into the sorption mode, in which by the sorption unit carbon dioxide and water is sorbed from the raw air of the enclosed air volume, b) switching of the other of the two sorption units by means of the air distribution device into the desorption mode in which, from the sorption unit, carbon dioxide and water are desorbed into the supplied regeneration air, and c) alternately performing the steps a) and b) in such a way that one of the two sorption units is operated in the sorption mode while the other one of the two sorption units is operated in the desorption mode. Preferably, the steps a) and b) are performed simultaneously. The features and embodiments which have been disclosed for the device apply likewise also to the method and vice versa.

In embodiments, heat is introduced into the sorption unit which is operated in the desorption mode. As mentioned before, for this purpose heating elements can be provided. However, the heat can be introduced also as waste heat of an electric motor.

In embodiments, in the enclosed air volume the carbon dioxide and water content is measured in order to control the device such that the carbon dioxide and water content in the enclosed air volume is kept in a predetermined tolerance field. For this purpose, a sensor or a plurality of sensors can be provided in the enclosed air volume. Also, the device itself comprises preferably a plurality of different sensors.

In embodiments, an occupation state of the enclosed air volume with passengers is detected in order to control the device in such a way that the carbon dioxide and water content in the enclosed air volume is kept in the predetermined tolerance field, independent of the occupation state. The occupation state can be detected, for example, by means of weight sensors or optical sensors. Energy can be saved due to the control based on the occupation state.

In embodiments, the desorption mode is performed with regeneration air which is removed from an environment of the enclosed air volume, with regeneration air which is removed from the enclosed air volume, or under vacuum. Under vacuum, the desorption mode can be performed preferably at lower temperatures. This results advantageously in energy savings. In case that the regeneration air is removed from the enclosed air volume, the regeneration air corresponds in particular to the raw air, which in this case is not saturated with carbon dioxide and water so that the raw air functioning as regeneration air can still take up carbon dioxide and water.

"One" is presently not to be understood to mandatorily be limiting to precisely one element. Instead also a plurality of elements, for example, two, three or more, can be provided. Also, any other numeral employed here is not to be understood such that an exact limitation to precisely the corresponding number of elements must be realized. Instead, deviations in numbers up and down are possible.

BRIEF DESCRIPTION OF THE DRAWINGS

In the Figures, same or functionally the same elements, if nothing to the contrary is mentioned, have been provided with same reference characters.

PREFERRED EMBODIMENTS

Figure 1:
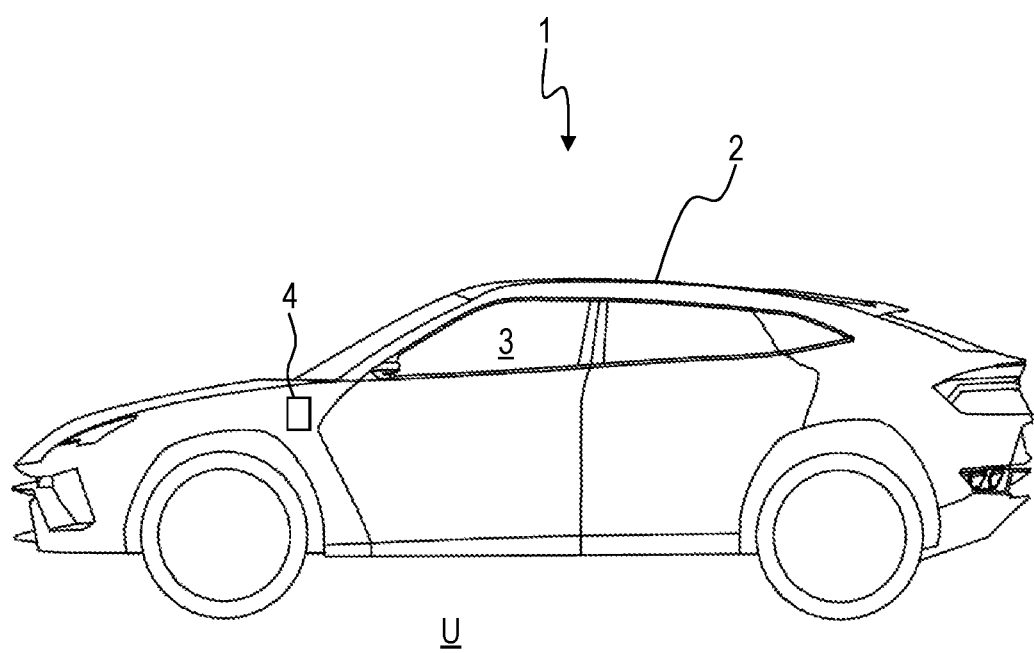
FIG. 1 shows a schematic view of an embodiment of a motor vehicle.

FIG. 1 shows a schematic view of an embodiment of a motor vehicle 1. The motor vehicle 1 is preferably an electric vehicle or a hybrid vehicle. The motor vehicle 1 can however be driven also by means of an internal combustion engine or a combustion motor. The motor vehicle 1 comprises a car body 2 enclosing an enclosed air volume 3. "Enclosed" means in this context that the car body 2 defines the boundaries or a geometric expansion of the enclosed air volume 3. This however does not mandatorily mean that the enclosed air volume 3 cannot be in air exchange with an environment U of the motor vehicle 1.

The enclosed air volume 3 is an interior or passenger compartment of the motor vehicle 1. The enclosed air volume 3 can however also be associated with a watercraft, a construction machine or a construction vehicle, a rail vehicle, an agricultural machine or an agricultural vehicle, or an aircraft. The enclosed air volume 3 can however also be part of a building or of a stationary machine.

In the following, it is however presumed that the enclosed air volume 3 is the passenger compartment of the motor vehicle 1. Therefore, the enclosed air volume 3 will be referred to in the following as passenger compartment. The passenger compartment 3 can be air-conditioned by means of an air conditioning device 4 (English: heating, ventilation, and air conditioning, HVAC). For extending a range of such an electrically driven motor vehicle 1, an energy savings as large as possible is aimed at. In reference to the air conditioning device 4, this means that the latter, for the purpose of air conditioning the passenger compartment 3, should take in as little fresh air as possible from the environment U of the motor vehicle 1.

When using recirculated air removed from the passenger compartment 3 for air conditioning the passenger compartment 3, it is however possible that water ($H_2O$) that is contained in the exhalation air of occupants or passengers can accumulate in the passenger compartment 3 which leads to fogging of window panes, for example, of a windshield or of side windows, of the motor vehicle 1. This is to be prevented or at least to be reduced with respect to safety aspects. Moreover, also carbon dioxide ($CO_2$) that is contained in the exhalation air can accumulate in the passenger compartment 3. This can lead to loss of concentration or even health impairments of the occupants. This also is to be prevented or at least reduced with respect to safety aspects as well as with respect to health aspects.

Figure 2:
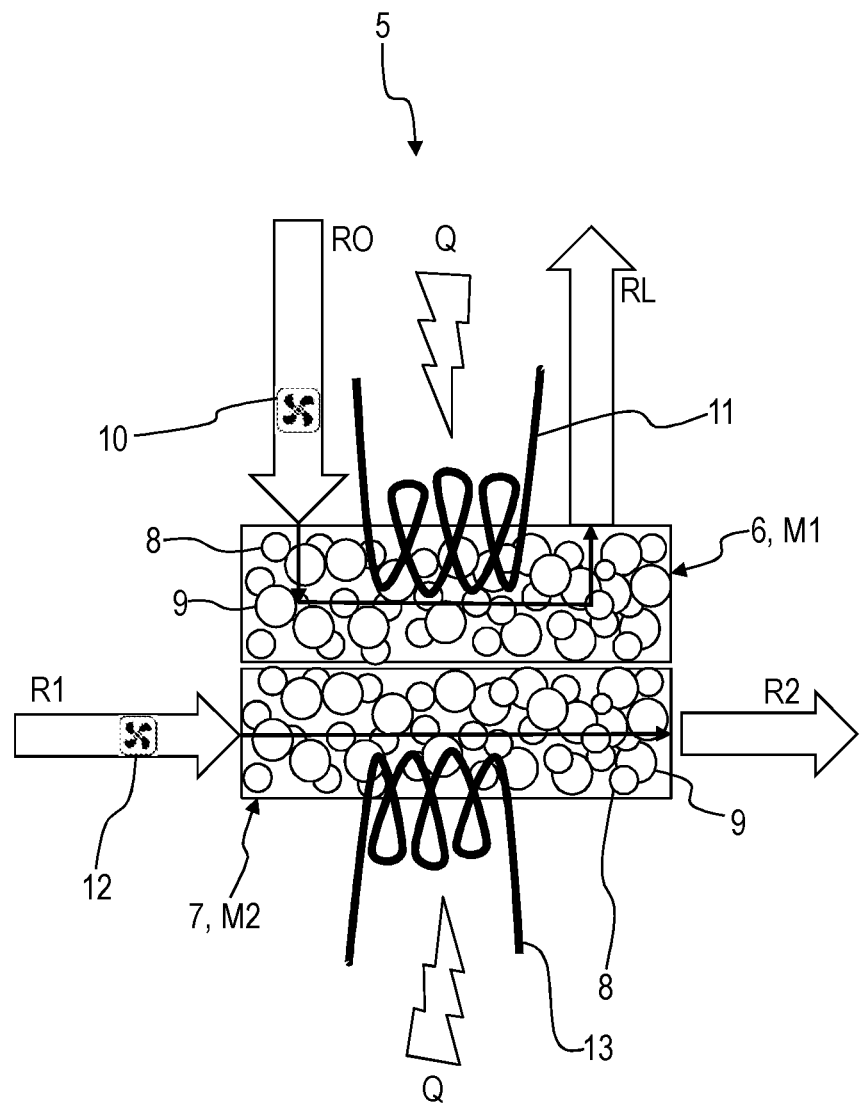
FIG. 2 shows a schematic view of an embodiment of a device for combined reduction of carbon dioxide and water for the vehicle.

FIG. 2 shows a schematic view of an embodiment of a device 5 for the combined reduction of $CO_2$ and $H_2O$, in particular water vapor, within the passenger compartment 3.

By means of the device 5, the aforementioned disadvantages can be prevented or their effect at least reduced. Moreover, by means of the device 5, it can also be prevented that contaminants from the environment U reach the passenger compartment 3 because, due to the processing of the recirculating air, intake of ambient air can be dispensed with to a large extent.

The device 5 comprises a first sorption unit 6 as well as a second sorption unit 7. "Sorption" is a collective term for processes that lead to an accumulation of a substance within a phase or at a boundary surface between two phases. The accumulation within a phase is referred to more precisely as absorption, that at a boundary surface as adsorption. This means the sorption units 6, 7 are suitable to adsorb and/or to absorb substances such as $CO_2$ and $H_2O$ but also nitrogen oxides (NOX) and/or volatile organic compounds (English: volatile organic compounds, VOCs). Examples of volatile organic compounds are higher hydrocarbons. The sorption units 6, 7 can also be suitable to adsorb and/or absorb sulfur dioxide ($SO_2$). Preferably, the sorption units 6, 7 are however pure adsorption units or can be referred to as such.

The sorption units 6, 7 are preferably exchangeable, and can be operated, as will be explained in the following, alternately in a sorption mode M1 and in a desorption mode M2. The sorption units 6, 7 are cartridge-shaped and can be referred to as cartridges or sorption cartridges. The sorption mode M1 can also be referred to as adsorption mode. The desorption mode M2 can also be referred to as regeneration mode. This means that the first sorption unit 6 is in the sorption mode M1 when the second sorption unit 7 is in the desorption mode M2 and vice versa. Thus, the two sorption units 6, 7 are never simultaneously in the same mode M1, M2. Preferably, the sorption units 6, 7 each comprise a cartridge form so that they are easily exchangeable.

Each sorption unit 6, 7 comprises a first sorbent 8 and a second sorbent 9. Preferably, the sorbents 8, 9 are adsorbents or can be referred to as such. For example, the first sorbent 8 is suitable to adsorb $CO_2$. Accordingly, the second sorbent 9 can be suitable to adsorb $H_2O$. The two sorbents 8, 9 can thus remove $H_2O$ and $CO_2$ from the passenger compartment 3. The first sorbent 8 is illustrated with small circles. The second sorbent 9 is illustrated with large circles. It is also possible to provide further sorbents that are suitable, for example, to sorb NOX or VOCs. Thus, an arbitrary number of different sorbents 8, 9 can be provided for processing the recirculated air in the passenger compartment 3.

For example, in addition to the sorbents 8, 9, at least one further sorbent or also a plurality of further sorbents (not illustrated) are provided that are suitable to remove fine particles, NOx and/or VOCs from the raw air RO. The further sorbents can be introduced between two carrier layers, in particular carrier layers of a nonwoven. Alternatively, the sorbents 8, 9 and the further sorbents can be mixed with each other. The further sorbents can comprise active carbon which, in particular in form of a bulk material, is introduced preferably between the two carrier layers. The further sorbent or the further sorbents can be mixed with the first sorbent 8 and/or with the second sorbent 9 in order to construct one or a plurality of mixed bulk materials.

Furthermore, the sorption units 6, 7 can also be suitable to remove, aside from $CO_2$ and $H_2O$, also allergens, bacteria and/or viruses from the raw air RO. This can be realized by a functional coating of carrier materials, for example, of nonwovens, or by a functional coating of the sorbents 8, 9. Moreover, the sorption units 6, 7 can comprise in regard to a comfort aspect at least one scent component.

The sorbents 8, 9 can each be in the form of spherical granular material. Preferably, the sorbents 8, 9 are fixed on a carrier material or fixed by means of a carrier material. The sorption units 6, 7 each can have a cylindrical, in particular a hollow cylindrical, a pie-shaped or a rectangular geometry. A "pie-shaped" geometry is to be understood presently in particular as a flat circular cylindrical geometry.

In FIG. 2, the first sorption unit 6 is in the aforementioned sorption mode M1. The second sorption unit 7 is in the desorption mode M2. In the sorption mode M1, the first sorption unit 6 is supplied with raw air RO from the passenger compartment 3 that is loaded with $CO_2$ and $H_2O$. For this purpose, a first blower device 10 can be provided. The raw air RO is at least in sections guided through the first sorption unit 6 wherein the sorbents 8, 9 purify the raw air RO from $CO_2$ and $H_2O$. The purified raw air RO is then returned to the passenger compartment 3 as clean air RL.

The first sorption unit 6 has correlated therewith an optional first heating element 11 with which the sorbents 8, 9 can be supplied with heat Q. In the sorption mode M1, the first heating element 11 is inactive so that it does not supply the first sorption unit 6 with heat Q. The first heating element 11 can be a heating wire which extends through the first sorption unit 6 and is supplied with current for introducing the heat Q and to thus heat the sorbents 8, 9. The heat Q can however be introduced also by any other way. For example, the heat Q can also be waste heat of an electric motor for driving the motor vehicle 1. The heat Q can also be waste heat of a conventional internal combustion engine, of a battery cooling system or of a fuel cell cooling circuit. The first heating element 11 can also be a heat exchanger or can comprise a heat exchanger.

In the desorption mode M2, the second sorption unit 7 is supplied with regeneration air R1 which is not loaded with $CO_2$ and $H_2O$. For this purpose, a second blower device 12 can be used. That the non-loaded regeneration air R1 is "non-loaded" with $CO_2$ and $H_2O$ is to be understood such that the non-loaded regeneration air R1 is capable of taking up $CO_2$ and $H_2O$ stored in the second sorption unit 7. This means that the non-loaded regeneration air R1 can comprise a certain content of $CO_2$ and $H_2O$. However, the non-loaded regeneration air R1 is not saturated with $CO_2$ and $H_2O$. The non-loaded regeneration air R1 can be removed, for example, from the passenger compartment 3 or from the environment U.

Moreover, an optional second heating element 13 is also provided by means of which the second sorption unit 7 in the desorption mode M2 is heated and heat Q is thus introduced into the second sorption unit 7. The first heating element 11 and the second heating element 13 are preferably of identical construction and are operated alternately. As mentioned before, the heat Q can be supplied, for example, also in the form of waste heat of an electric motor. The heat Q, as also mentioned before, can however also be waste heat of a conventional internal combustion engine, of a battery cooling system or of a fuel cell cooling circuit. The second heating element 13 can also be a heat exchanger or can comprise a heat exchanger.

Upon heating the sorbents 8, 9 in the desorption mode M2 of the second sorption unit 7, they release $CO_2$ and $H_2O$ into the non-loaded regeneration air R1. This means that $CO_2$ and $H_2O$ are desorbed. Preferably, a temperature of above 55° C. is required for desorption. The non-loaded regeneration air R1 is guided through the second sorption unit 7, there takes up $CO_2$ and $H_2O$, and is then discharged from the second sorption unit 7 as loaded regeneration air R2. In particular, the loaded regeneration air R2 is supplied to the environment U.

Figure 3:
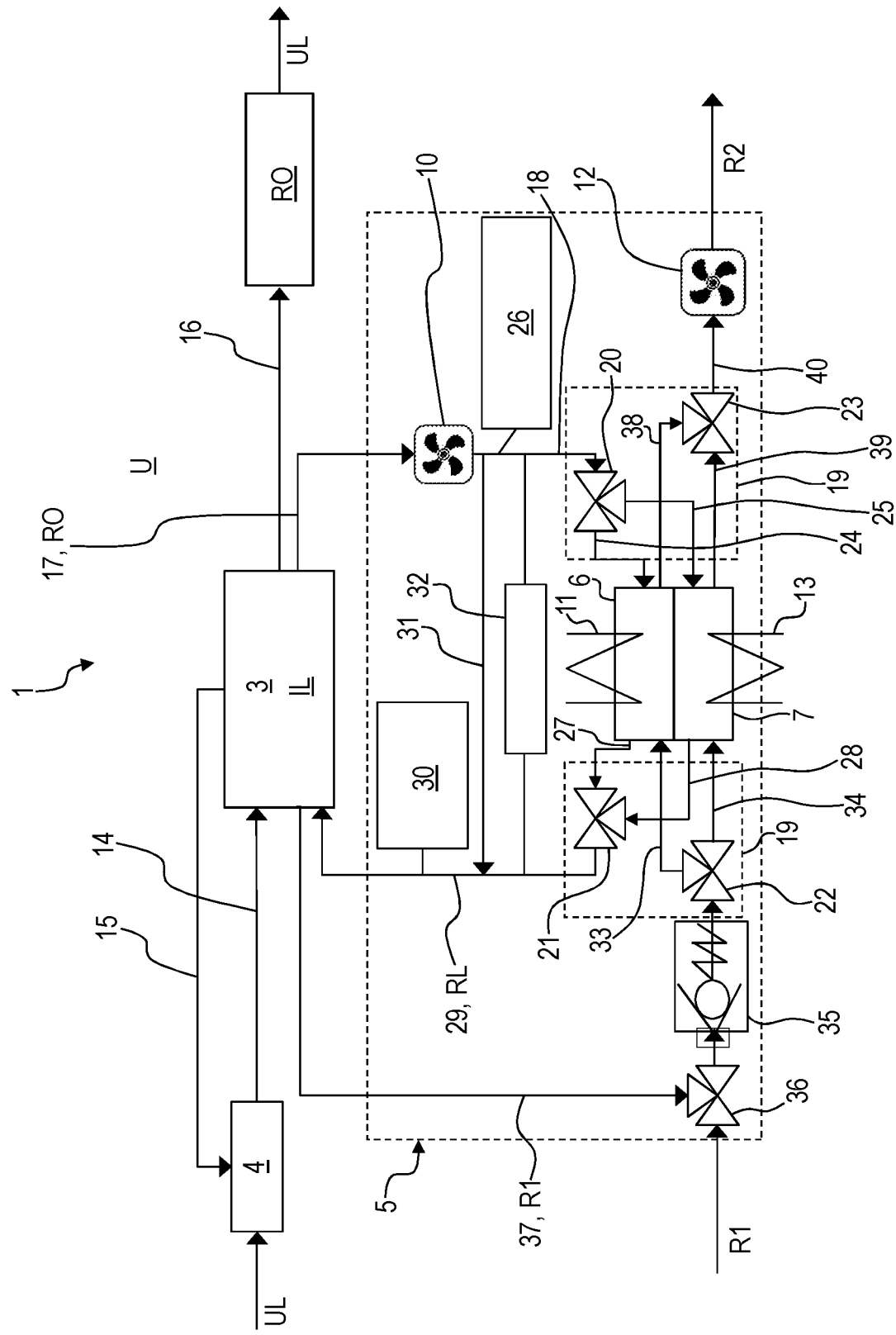
FIG. 3 shows a greatly simplified schematic view of the motor vehicle according to FIG. 1.

FIG. 3 shows a greatly schematic view of the motor vehicle 1 with the device 5. In this embodiment of the motor vehicle 1, the device 5 operates independent of the air conditioning device 4. Ambient air UL can be supplied via the air conditioning device 4 to the passenger compartment 3. By means of the air conditioning device 4, the ambient air UL can be temperature-controlled and purified from particulate matter, for example, dust or pollen. For this purpose, the air conditioning device 4 can have an interior filter. The purified and temperature-controlled ambient air UL is supplied to the passenger compartment 3 via conduit 14 as interior air IL. By means of a conduit 15, the interior air IL can be supplied again to the air conditioning device 4, for example, in order to heat or cool the interior air IL in recirculation operation.

In operation of the motor vehicle 1, the interior air IL in the passenger compartment 3 is loaded with $CO_2$ and $H_2O$. The loaded interior air IL is the aforementioned raw air RO. This aforementioned raw air RO can be supplied via a conduit 16 at least partially to the environment U. Moreover, the raw air RO loaded with $CO_2$ and $H_2O$ can be supplied by means of a conduit 17 at least partially to the device 5. In particular, the conduit 17 supplies the raw air RO to the first blower device 10. The first blower device 10 is mounted at the pressure side. The first blower device 10 can however also be mounted at the suction side.

Downstream of the first blower device 10, a conduit 18 is provided which supplies the raw air RO to an air distribution device 19. The air distribution device 19 comprises a plurality of valves 20 to 23, in particular three-way valves. The valves 20-23 are preferably embodied as flap valves. Accordingly, the air distribution device 19 can also be referred to as a flap device or flap system.

The conduit 18 is in fluid communication with the valve 20 that, in turn, is in fluid communication via conduits 24, 25 with the two sorption units 6, 7. Depending on the switched position of the valve 20, the raw air RO can be supplied selectively either to the first sorption unit 6 or to the second sorption unit 7. In or at the conduit 18, a sensor 26, in particular a $CO_2$, $H_2O$ and/or temperature sensor, can be provided. In particular, the conduit 24 connects the valve 20 to the first sorption unit 6. The conduit 25 connects the valve 20 to the second sorption unit 7.

Downstream of the sorption units 6, 7, a valve 21 of the air distribution device 19 is provided. The valve 21 is connected by means of a conduit 27 to the first sorption unit 6 and by means of a conduit 28 to the second sorption unit 7. A conduit 29 connects the valve 21 to the passenger compartment 3. The conduit 29 can also comprise a sensor 30, in particular a $CO_2$, $H_2O$ and/or temperature sensor. By means of the sensor 30, it can be detected, for example, when the sorption unit 6, 7 which is in the sorption mode M1 is exhausted. Between the conduits 18, 29 a bypass conduit 31 for bypassing the sorption units 6, 7 is provided. Moreover, between the conduits 18, 29, a sensor 32, in particular pressure sensor, is provided also which can detect a pressure difference between the conduits 18, 29.

The air distribution device 19 comprises a further valve 22 which by means of a conduit 33 is connected to the first sorption unit 6 and by means of the conduit 34 to the second sorption unit 7. A check valve 35 as well as a regeneration valve 36 are arranged upstream of the valve 22. The regeneration valve 36 is preferably a three-way valve. The ambient air UL is supplied to the regeneration valve 36 as non-loaded regeneration air R1. Moreover, the interior air IL as non-loaded regeneration air R1 can also be supplied to the regeneration valve 36 via a conduit 37.

Downstream of the sorption units 6, 7, a further valve 23 of the air distribution device 19 is positioned. The valve 23 is connected by means of a conduit 38 to the first sorption unit 6 and by means of a conduit 39 to the second sorption unit 7. A conduit 40 connects the valve 23 to the second blower device 12. The second blower device 12 is positioned in this context at the suction side, i.e., downstream of the sorption units 6, 7. The second blower device 12 can however also be positioned at the pressure side, i.e., upstream of the sorption units 6, 7. The second blower device 12 discharges the loaded regeneration air R2 into the environment U.

Figure 4:
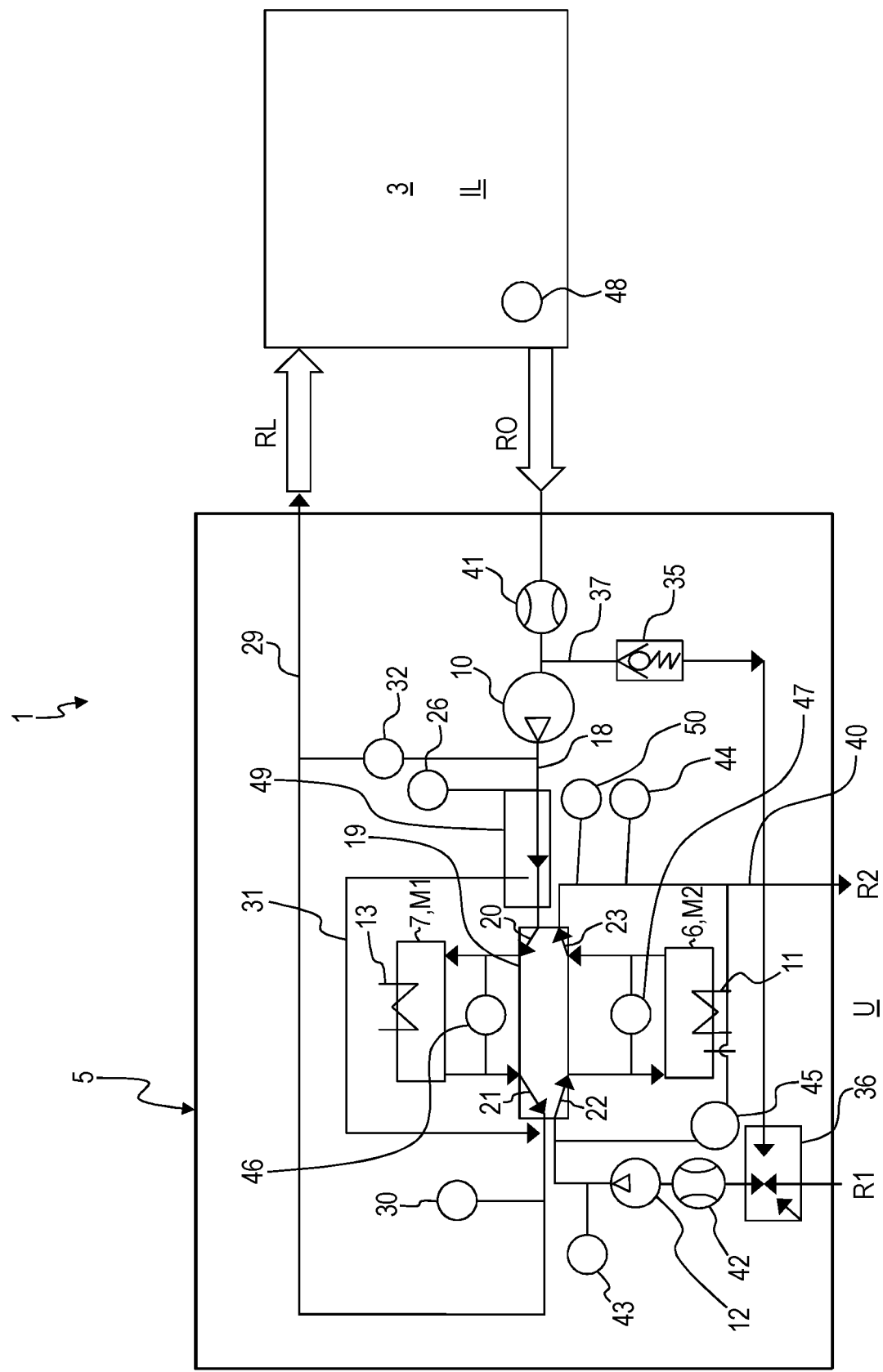
FIG. 4 shows a further greatly simplified schematic view of the motor vehicle according to FIG. 1.

FIG. 4 shows the motor vehicle 1 in an operating state of the device 5 in which the first sorption unit 6 is in the desorption mode M2 and the second sorption unit 7 in the sorption mode M1. In contrast to FIG. 3, both blower devices 10, 12 are positioned at the pressure side. A volume flow sensor 41 can be arranged upstream of the first blower device 10. A volume flow sensor 42 is also provided downstream of the regeneration valve 36.

Downstream of the second blower device 12, a further sensor 43, in particular a $CO_2$, $H_2O$ and/or temperature sensor, is provided. Moreover, a further sensor 44, in particular a $CO_2$, $H_2O$ and/or temperature sensor, is also provided in or at the conduit 40. Moreover, a sensor 45 is provided which is suitable to detect a pressure difference between the conduit 40 and the air distribution device 19. Each sorption unit 6, 7 has correlated therewith a sensor 46, 47, in particular a differential pressure sensor. Also, a sensor 48, in particular as $CO_2$, $H_2O$ and/or temperature sensor, can be provided in the passenger compartment 3. In order to activate and deactivate the bypass conduit 31, a bypass valve 49 is provided. Moreover, the conduit 40 comprises a pressure sensor 50, in particular for determining the absolute pressure.

In FIG. 4 the regeneration valve 36 is switched such that the non-loaded regeneration air R1 is taken in from the environment U and not from the passenger compartment 3. The valves 22, 23 are switched such that the non-loaded regeneration air R1 is pressed by means of the second blower device 12 arranged at the pressure side through the first sorption unit 6. In this context, the first heating element 11 is in operation. The first sorption unit 6 releases $CO_2$ and $H_2O$ to the non-loaded regeneration air R1 which is then supplied as loaded regeneration air R2 into the environment U.

At the same time, the valves 20, 21 are switched such that by means of the first blower device 10 raw air RO loaded with $CO_2$ and $H_2O$ is sucked in from the passenger compartment 3 and guided through the second sorption unit 7. In the second sorption unit 7, the $CO_2$ in the $H_2O$ are adsorbed and the non-loaded clean air RL is supplied again to the passenger compartment 3. The bypass valve 49 is switched such that the bypass conduit 31 is inactive.

Figure 5:
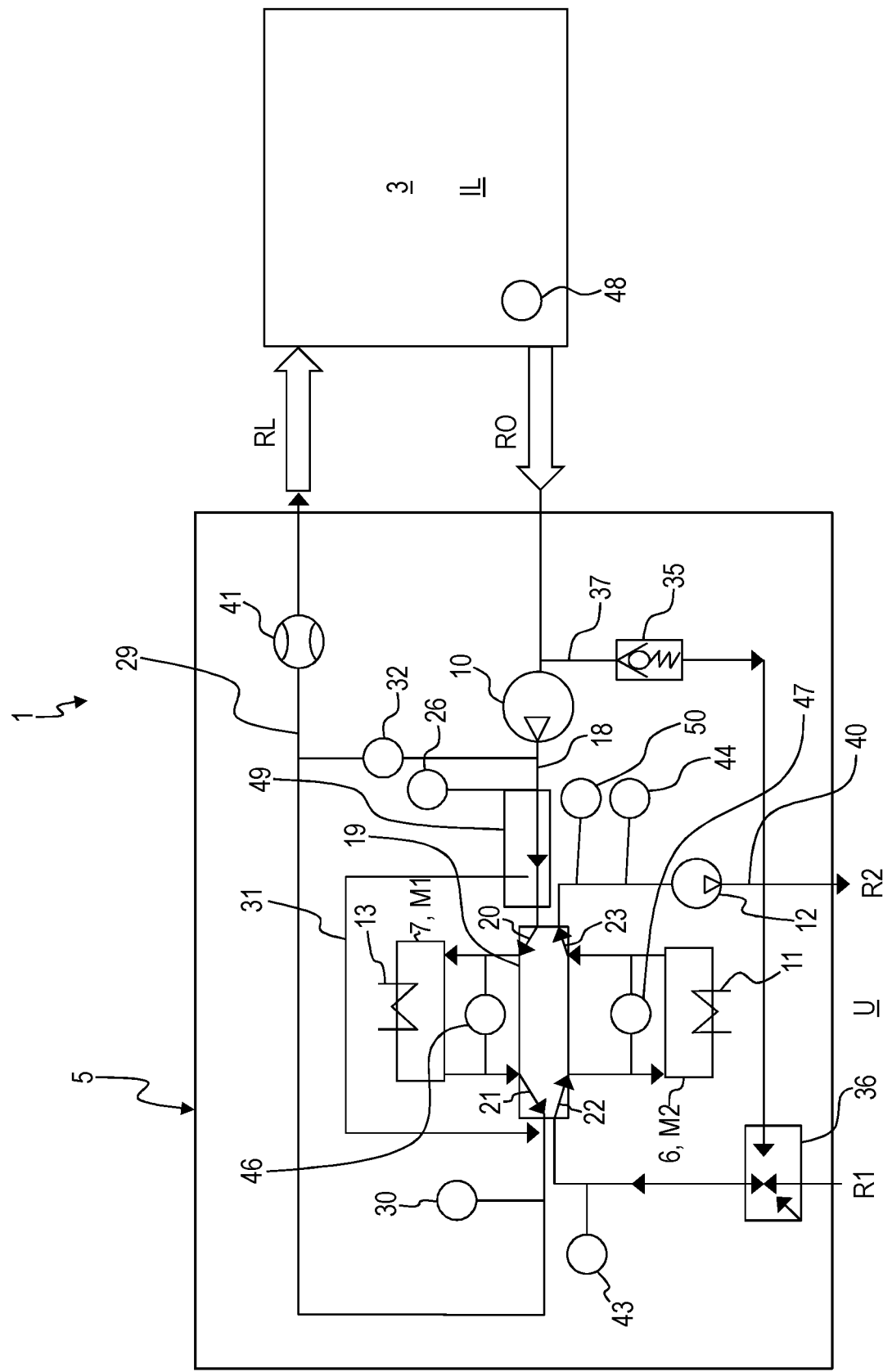
FIG. 5 shows a further greatly simplified schematic view of the motor vehicle according to FIG. 1.

FIG. 5 shows a motor vehicle 1 in a further embodiment of the device 5. In this context, the first sorption unit 6 is in the desorption mode M2 and the second sorption unit 7 in the sorption mode M1 in FIG. 5. The device 5 according to FIG. 5 differs from the device 5 according to FIG. 4 substantially in that the second blower device 12 is not positioned at the pressure side but at the suction side. "Suction side" means in this context downstream of the sorption units 6, 7.

Figure 6:
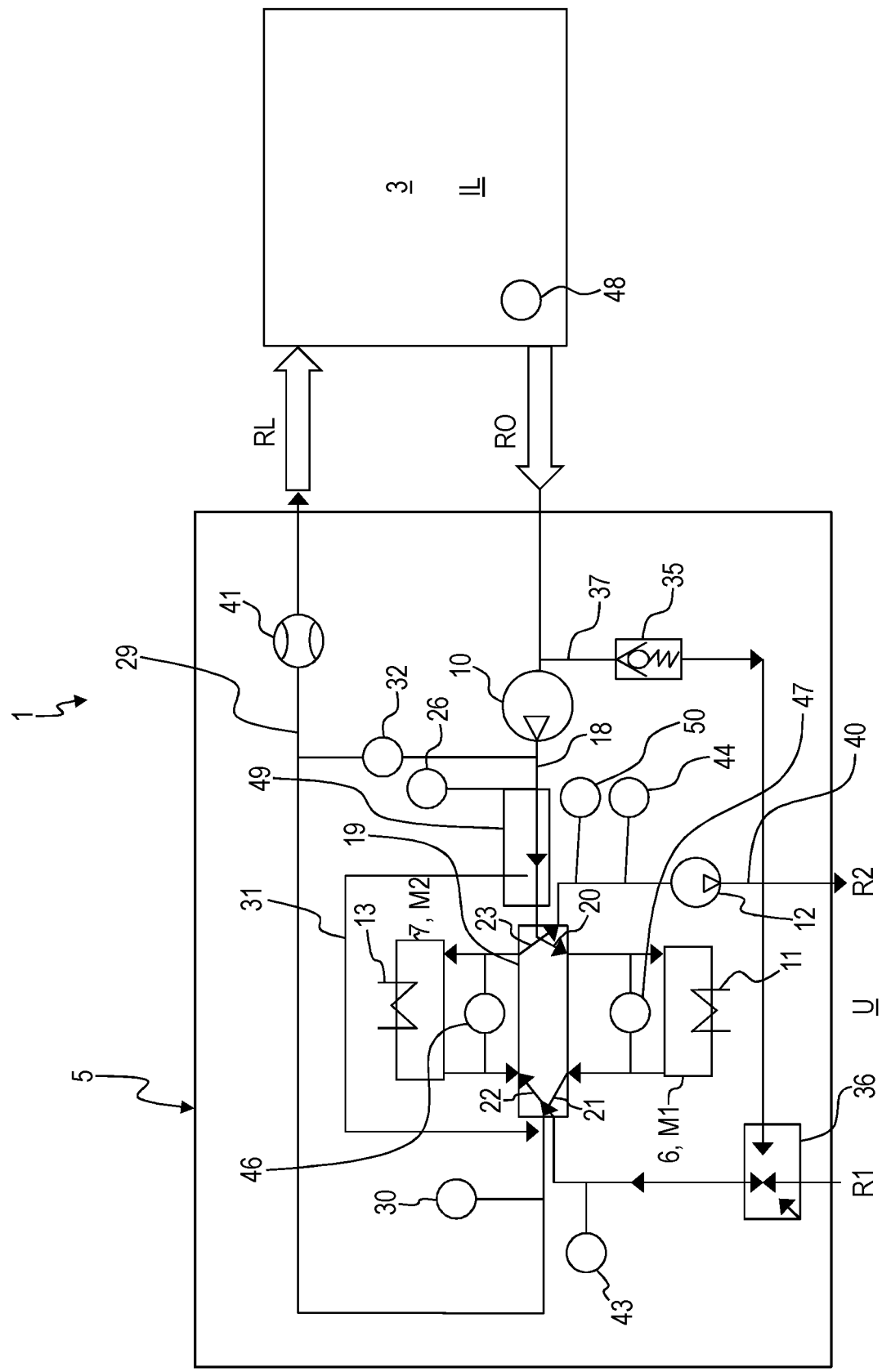
FIG. 6 a further greatly simplified schematic view of the motor vehicle according to FIG. 1.

FIG. 6 shows the device 5 according to FIG. 5, wherein the first sorption unit 6 is in the sorption mode M1 and the second sorption unit 7 in the desorption mode M2 is provided. The regeneration valve 36 is still switched such that the non-loaded regeneration air R1 is taken in from the environment U. The valves 20, 21 of the air distribution device 19 are switched such that by means of the first blower device 10 raw air RO that is enriched with $CO_2$ and $H_2O$ and sucked in from the passenger compartment 3 is guided through the first sorption unit 6 and is supplied again as clean air RL from which $CO_2$ and $H_2O$ has been removed to the passenger compartment 3. The bypass conduit 31 is inactive.

The valves 22, 23 are switched such that the non-loaded regeneration air R1 taken in from the environment U is sucked by means of the second blower device 12 through the second sorption unit 7. The second heating element 13 is in operation in this context. The second blower device 12 blows the regeneration air R2 which is enriched with CO2 and H2O into the environment U.

Figure 7:
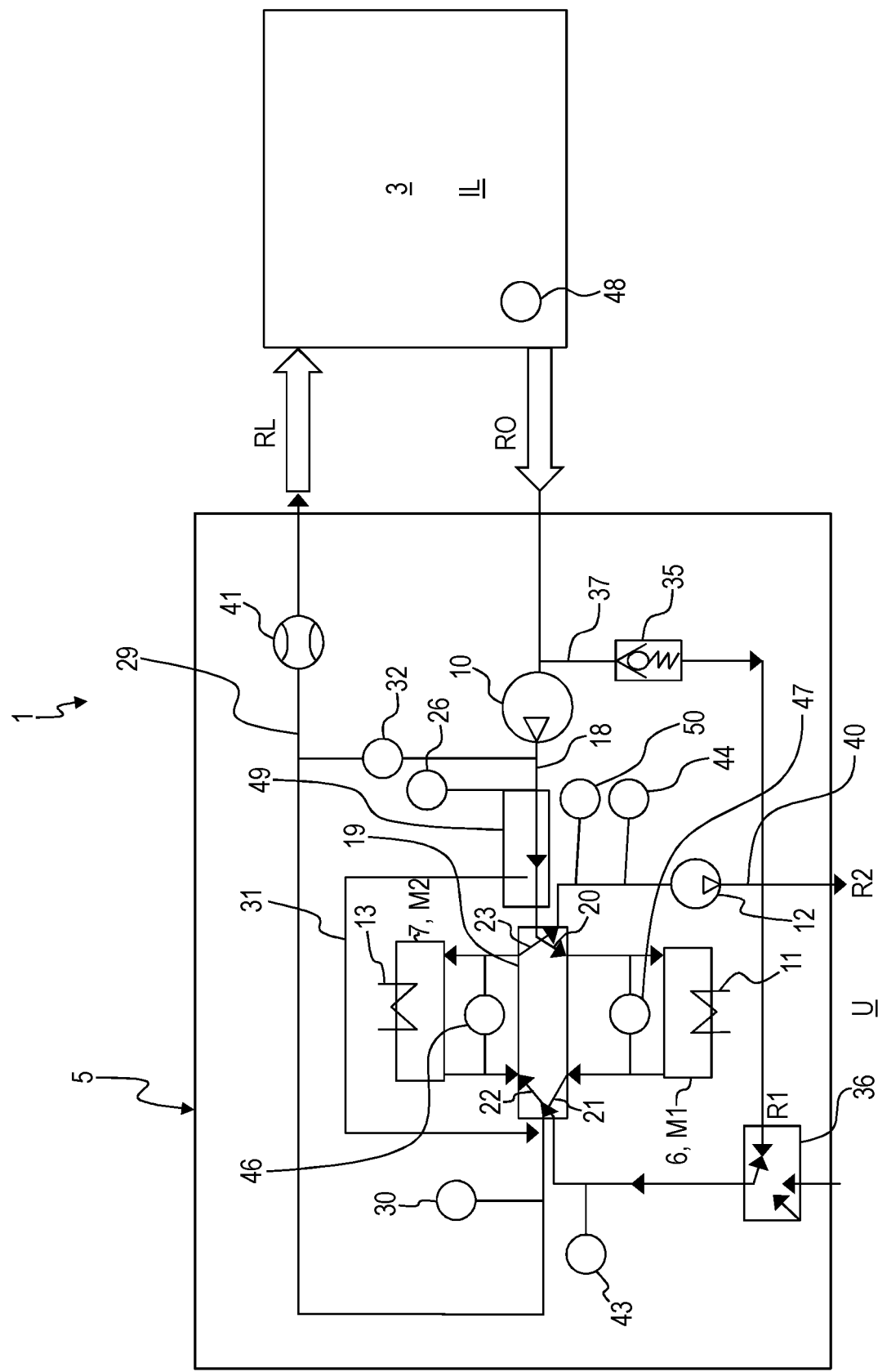
FIG. 7 shows a further greatly simplified schematic view of the motor vehicle according to FIG. 1.

FIG. 7 shows again the device 5 according to FIGS. 5 and 6. In this context, the first sorption unit 6 is in sorption mode M1 and the second sorption unit 7 in desorption mode M2. In contrast to FIG. 6, the regeneration valve 36 is switched however such that the raw air RO from the passenger compartment 3 is employed as non-loaded regeneration air R1. This means the non-loaded regeneration air R1 is not taken in from the environment U.

Figure 8:
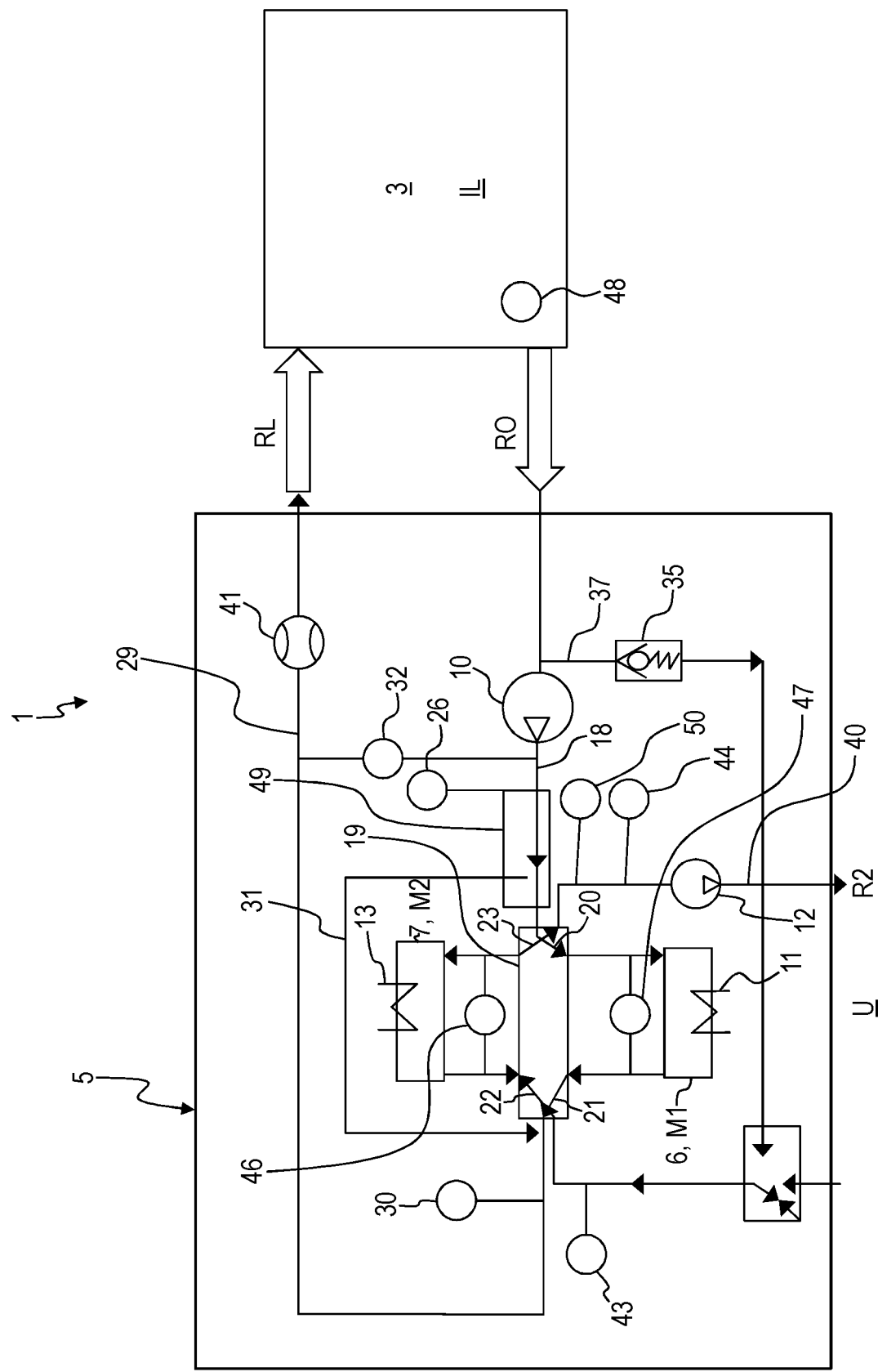
FIG. 8 a further greatly simplified schematic view of the motor vehicle according to FIG. 1.

FIG. 8 shows again the device 5 according to FIGS. 5 and 6. In this context, the first sorption unit 6 is in the sorption mode M1 and the second sorption unit 7 is in the desorption mode M2. In contrast to FIG. 6, the regeneration valve 36 is however switched such that neither from the environment U nor from the passenger compartment 3 non-loaded regeneration air R1 is taken in. Instead, the desorption mode M2 of the second sorption unit 7 is carried out under vacuum or negative pressure generated by means of the second blower device 12. The bypass valve 31 is inactive in this context.

Figure 9:
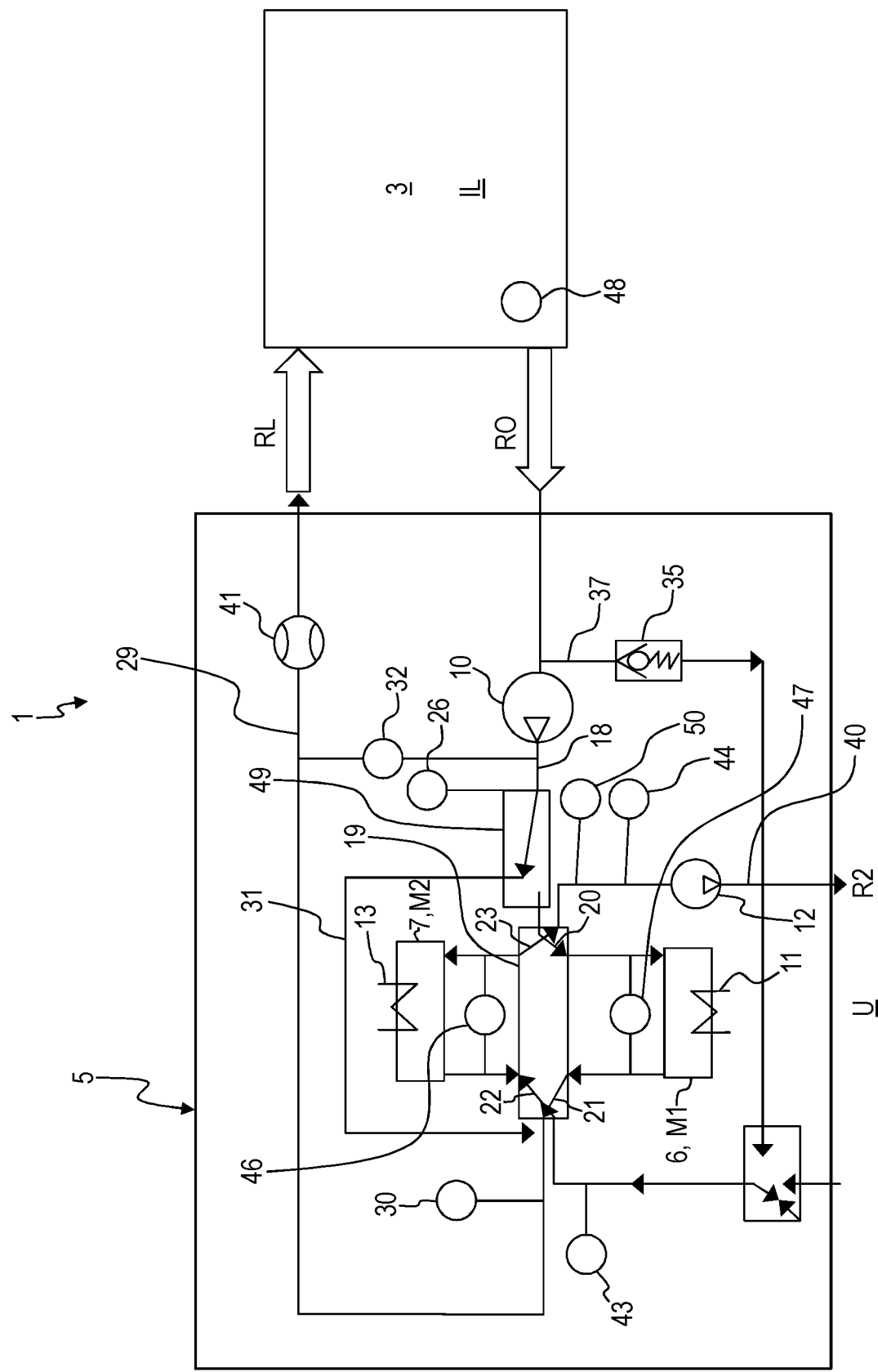
FIG. 9 shows a further greatly simplified schematic view of the motor vehicle according to FIG. 1.

FIG. 9 shows again the device 5 according to FIGS. 5 and 6. In this context, the first sorption unit 6 is in the sorption mode M1 and the second sorption unit 7 in the desorption mode M2. In contrast to FIG. 8, the bypass valve 49 is however switched such that the bypass conduit 31 is active. This means that raw air RO from the passenger compartment 3 is guided past the sorption units 6, 7. The air of the bypass conduit 31 is returned via the conduit of the clean air RL into the passenger compartment. In the desorption mode M2, the second sorption unit 7 is under vacuum or negative pressure, as has been explained before in relation to FIG. 8.

Figure 10:
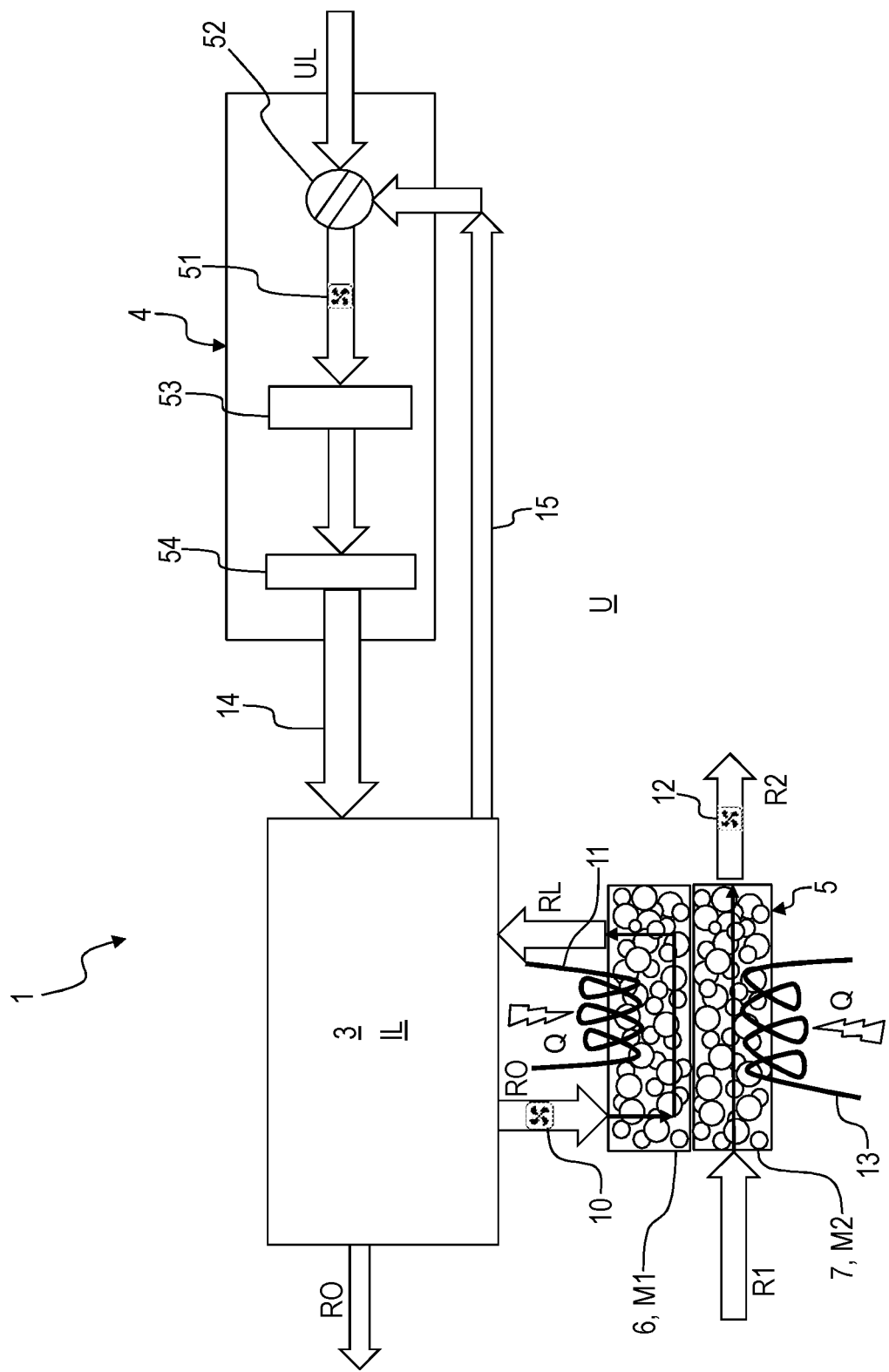
FIG. 10 shows a greatly simplified schematic view of a further embodiment of a motor vehicle.

FIG. 10 shows a further embodiment of the motor vehicle 1 in which the device 5 is operating independent of the air conditioning device 4 and is thus not integrated therein. The device 5 operates thus self-sufficiently and can be installed, for example, as a self-sufficient module in the motor vehicle 1. No direct interface is provided between the device 5 and the air conditioning device 4. The air conditioning device 4 comprises its own blower device 51 that is suitable to suck in, to temperature-control and/or to purify ambient air UL from the environment or interior air IL from the passenger compartment 3.

Furthermore, the air conditioning device 4 comprises a valve 52, for example, a flap valve, that can be switched such that either ambient air UL from the environment U or interior air IL from the passenger compartment 3 is sucked in. For temperature control, a cooling element 53 and a heating element 54 are provided. Moreover, the air conditioning device 4 can also comprise a filter element, not illustrated, for example, in the form of an interior filter.

Figure 11:
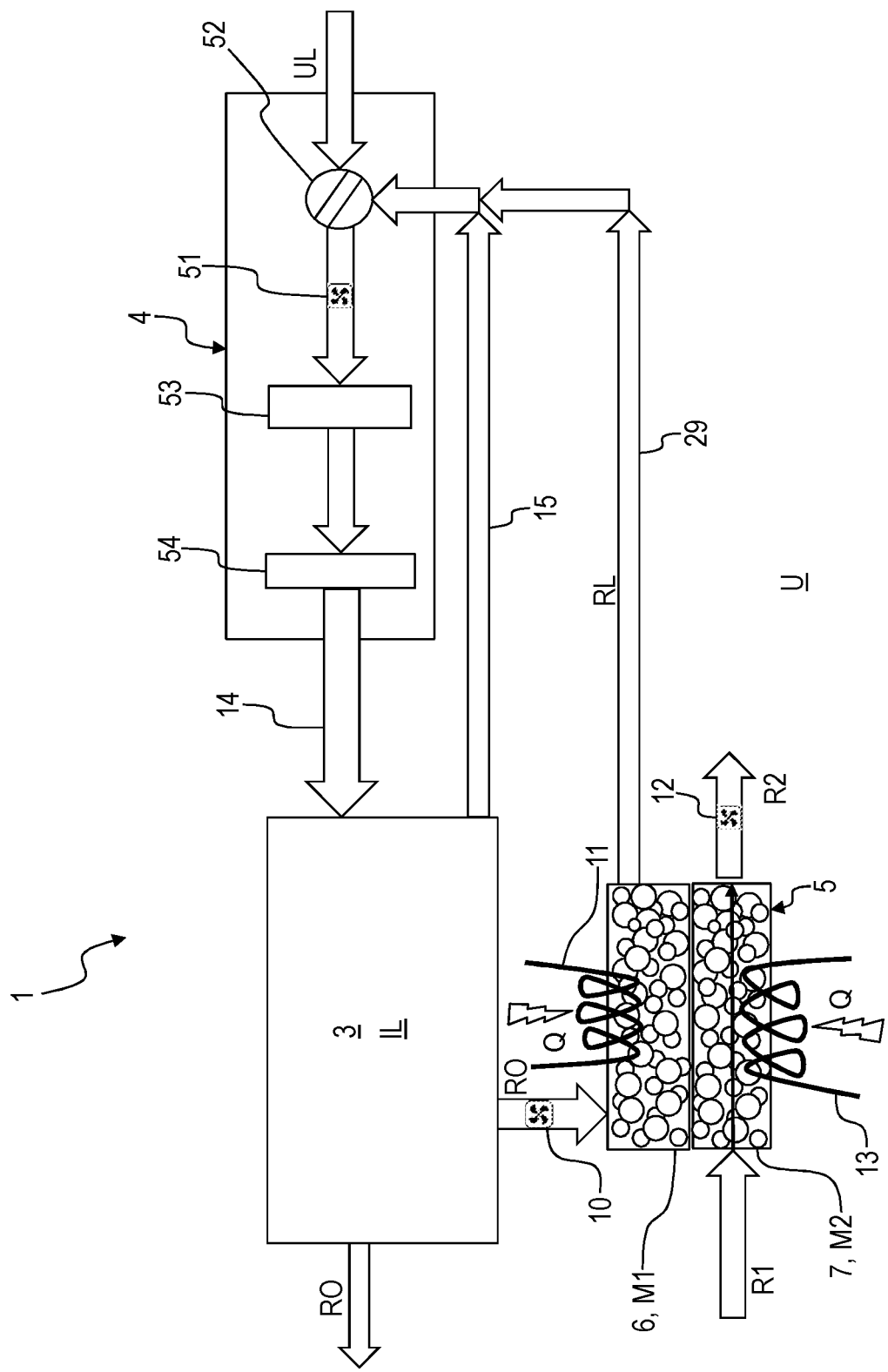
FIG. 11 shows a greatly simplified schematic view of a further embodiment of a motor vehicle.

FIG. 11 shows a further embodiment of the motor vehicle 1 in which the device 5 is partially integrated into the air conditioning device 4. Here, the conduit 29 which guides the clean air RL away from the sorption units 6, 7 is not connected directly to the passenger compartment 3 but to the air conditioning device 4, in particular to the conduit 15 which serves for recirculating operation of the air conditioning device 4. In this way, a very simple interface between the device 5 and the air conditioning device 4 is possible.

This means in particular that the clean air RL is not directly guided into the passenger compartment 3 but through the air conditioning device 4 into it. In this way, for example, it is possible to temperature-control the clean air RL from which $CO_2$ and $H_2O$ has been removed. This means that a portion of the interior air IL is passed as raw air RO through the first sorption unit 6 and a further portion of the interior air IL is guided in recirculation operation through the air conditioning device 4. The device 5 as well as the air conditioning device 4 comprise their own blower devices 10, 12, 51 which however can be synchronized.

Figure 12:
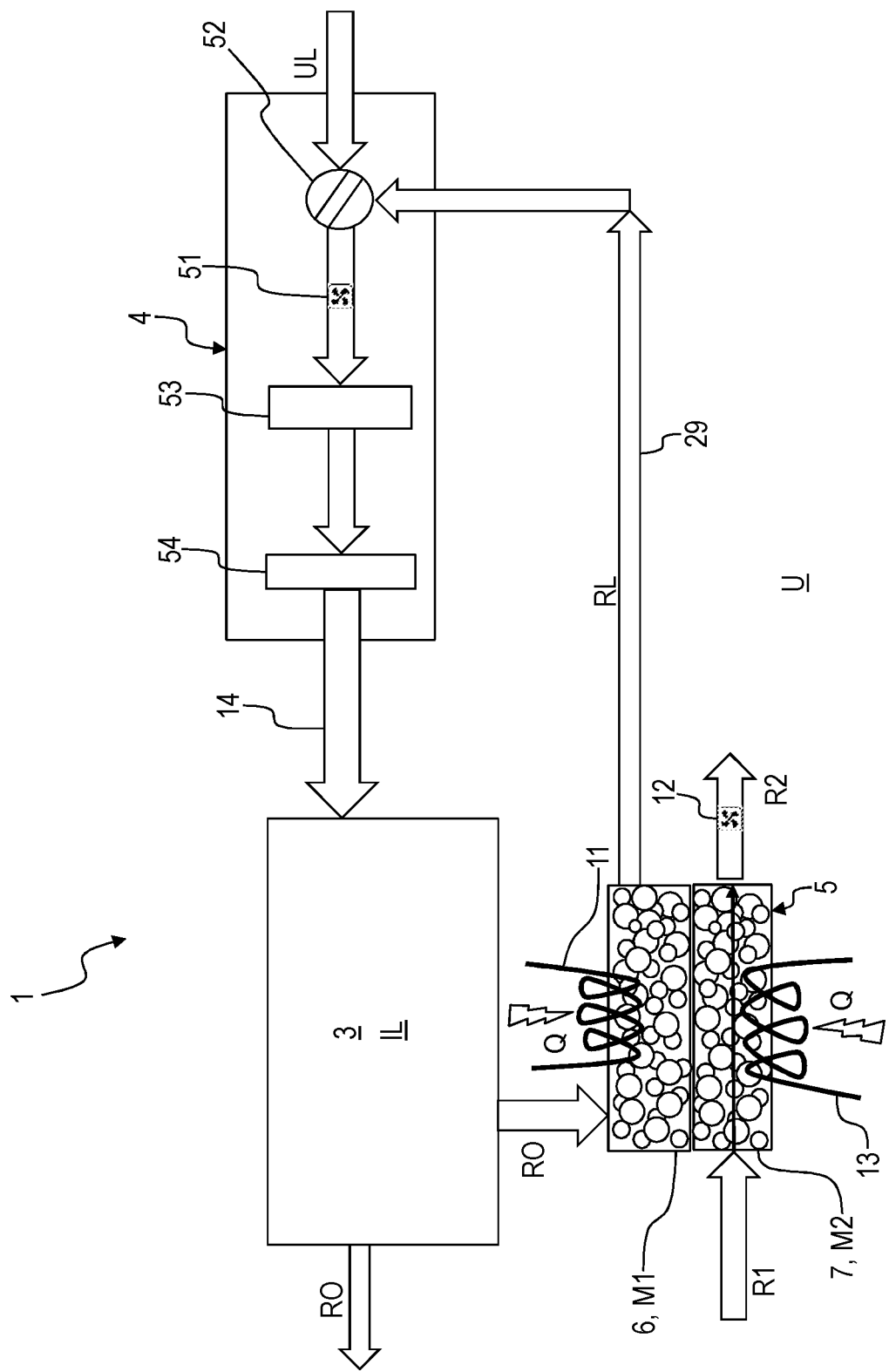
FIG. 12 shows a greatly simplified schematic view of a further embodiment of a motor vehicle.

FIG. 12 shows a further embodiment of the motor vehicle 1, in which the device 5 is fully integrated into the air conditioning device 4. In this embodiment of the device 5, the first blower device 10 can be dispensed with because in the sorption mode M1 the blower device 51 of the air conditioning device 4 can be used for passing the raw air RO through the corresponding sorption unit 6, 7. For this purpose, the conduit 29 which guides the clean air RL away from the sorption units 6, 7 is connected directly to the valve 52 of the air conditioning device 4.

Figure 13:
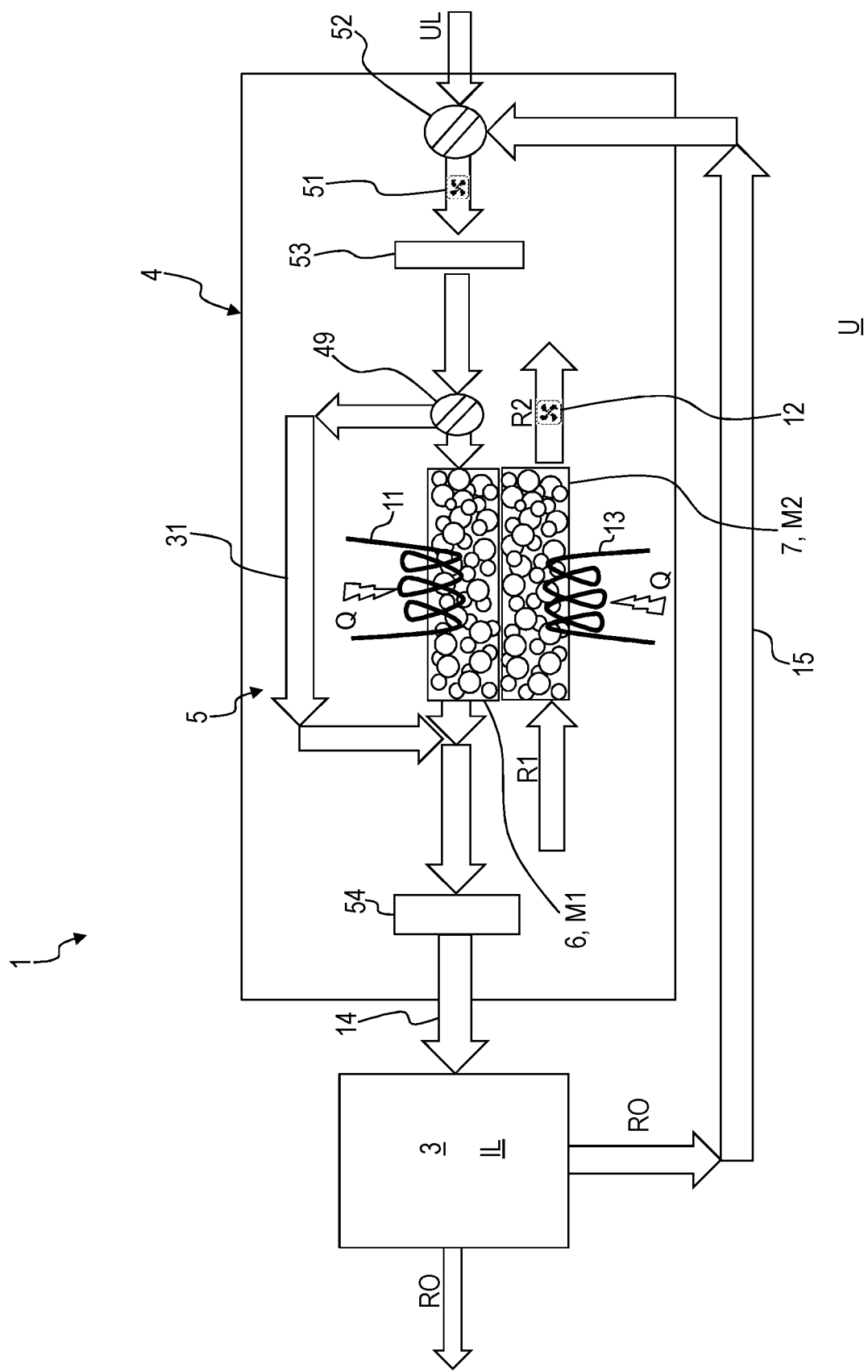
FIG. 13 shows a greatly simplified schematic view of a further embodiment of a motor vehicle.

FIG. 13 also shows a further embodiment of the motor vehicle 1 in which the device 5 is fully integrated into the air conditioning device 4. In this embodiment of the device 5, the first blower device 10 can be dispensed with. In this context, the bypass conduit 31 and the bypass valve 49 are also integrated into the air conditioning device 4. It is thus possible to suck in ambient air UL taken in from the environment U by means of the blower device 51 and, depending on the switched state of the bypass valve 49, to guide it completely around the sorption units 6, 7 or completely or partially guide it through one of the sorption units 6, 7.

Figure 14:
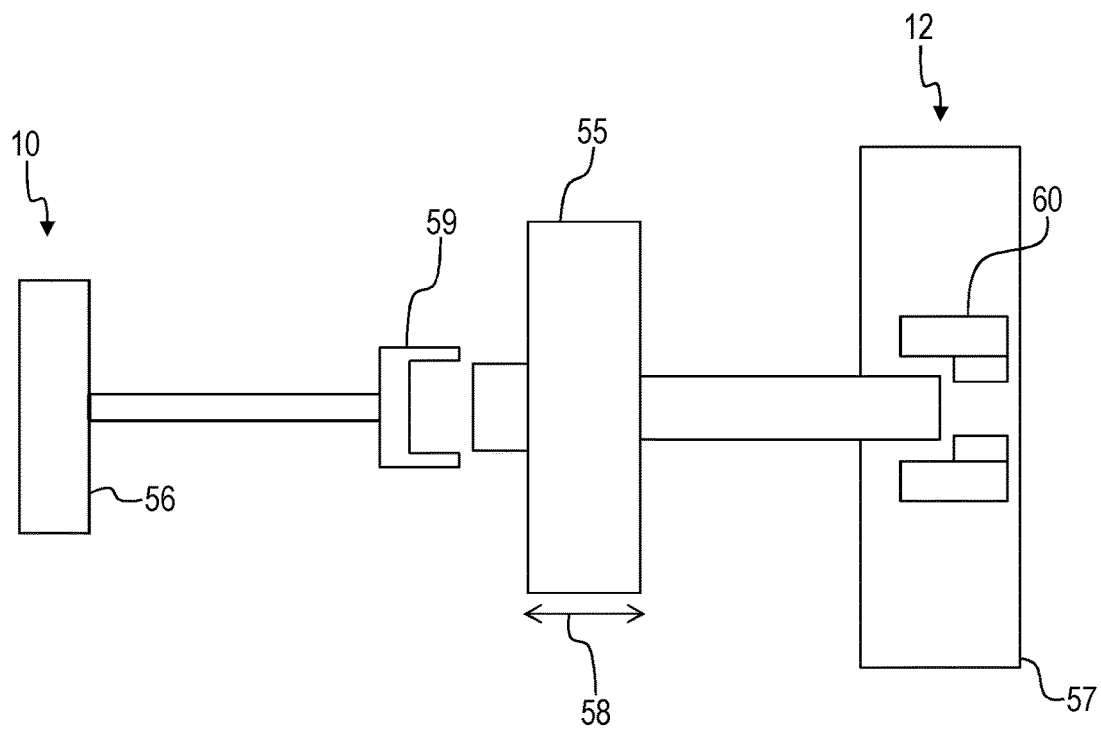
FIG. 14 shows a schematic view of an embodiment of a blower device for the device according to FIG. 2.

As illustrated in FIG. 14, the two blower devices 10, 12 of the device 5 can be driven by a common drive element 55, for example, by an electric motor. In this context, the first blower device 10 has correlated therewith a first blower wheel 56 and the second blower device 12 a second blower wheel 57. The drive element 55, as indicated by means of an arrow 58, can be linearly displaceable in order to couple the drive element 55 selectively with the blower wheels 56, 57 or decouple it therefrom.

The drive element 55 comprises in this context three switch positions. In a first switch position, only the second blower wheel 57 is driven, in a second switch position, both blower wheels 56, 57 are driven, and in a third switch position only the first blower wheel 56 is driven. Between the first blower wheel 56 and the drive element 55, a first coupling 59 can be provided that is suitable to couple the drive element 55 with the first blower wheel 56 or to decouple it from the drive element 55. Between the second blower wheel 57 and the drive element 55, a second coupling 60 can be provided that is suitable to couple the drive element 55 with the second blower wheel 57 or to decouple it from the drive element 55.

Figure 15:
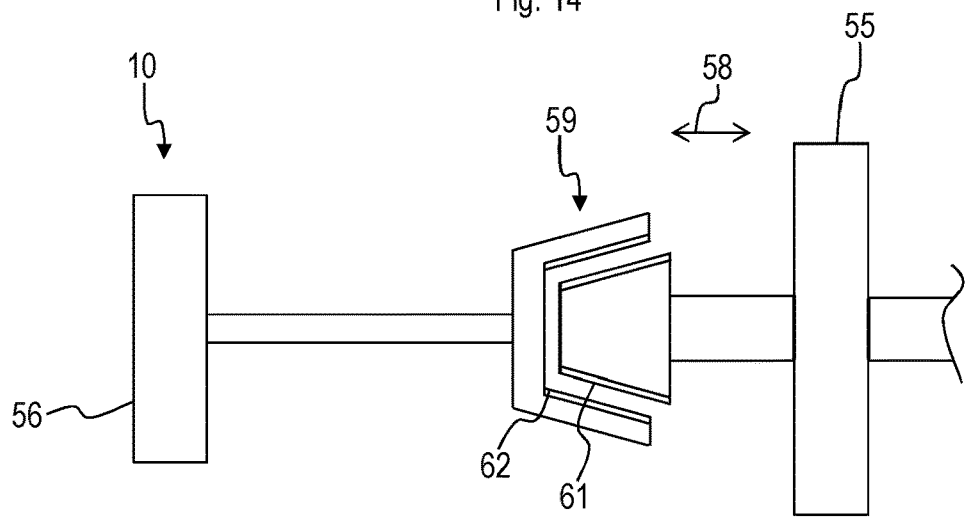
FIG. 15 shows a schematic view of a further embodiment of a blower device for the device according to FIG. 2.

As illustrated in FIG. 15, the first coupling 59 can be embodied as a cone-shaped gear mechanism with two cone-shaped gear wheels 61, 62. In this context, the gear wheel 61 is correlated with the drive element 55 and the gear wheel 62 is correlated with the first blower wheel 56. By axial displacement of the drive element 55, the gear wheels 61, 62 can be brought into form fit engagement and disengaged again. The second coupling 60 can be constructed identically to the first coupling 59.

Figure 16:
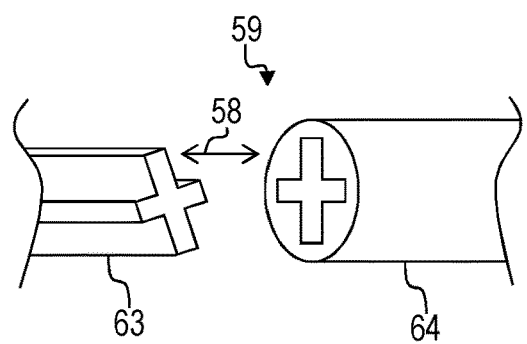
FIG. 16 shows a schematic view of an embodiment of a coupling for the blower device according to FIG. 14.

As illustrated in FIG. 16, the couplings 59, 60 can also be designed as cross-shaped gear mechanisms. In this case, the respective coupling 59, 60 can comprise two cross shafts 63, 64, respectively, which can be inserted into each other and pulled apart from each other in order to couple the drive element 55 to the respective blower wheel 56, 57 or to decouple the respective blower wheel 56, 57 from the drive element 55.

Figure 17:
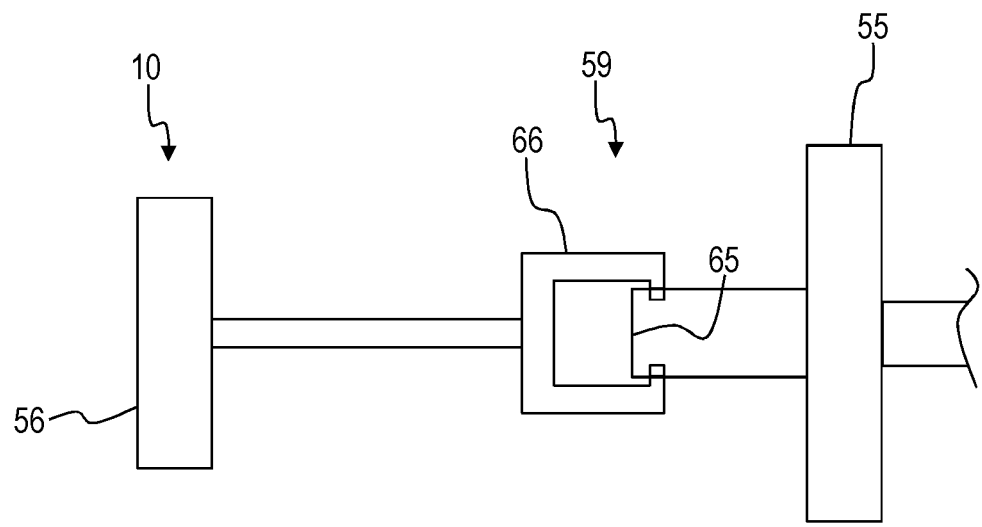
FIG. 17 shows a schematic view of a further embodiment of a blower device for the device according to FIG. 2.
Figure 18:
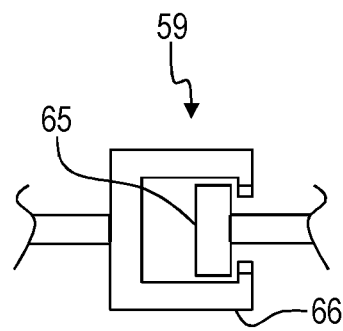
FIG. 18 shows a schematic view of an embodiment of a coupling for the blower device according to FIG. 17.

As illustrated in FIGS. 17 and 18, an actuated coupling 59, 60 with a first coupling element 65 and a second coupling element 66 can be provided also, respectively. The coupling elements 65, 66 can be actuated by means of an actuator, not illustrated, in order to connect to each other or disconnect from each other the coupling elements 65, 66. By means of the use of the couplings 59, 60, it is thus possible to save a drive element 55.

Figure 19:
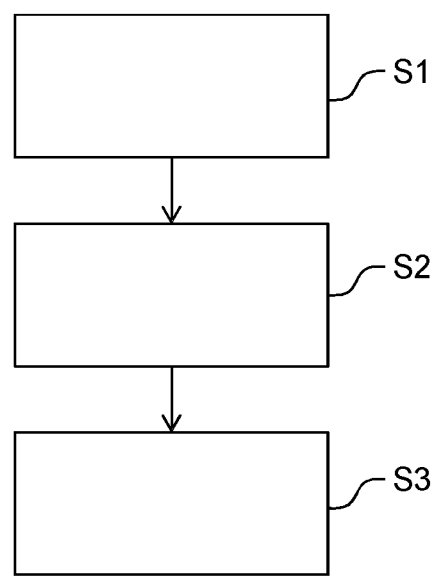
FIG. 19 shows a schematic block diagram of an embodiment of a method for operating the device according to FIG. 2.

FIG. 19 shows a schematic block diagram of a method for operating the afore explained device 5. The method comprises the steps explained in following. In a step S 1, one of the two sorption units 6, 7, for example, the first sorption unit 6, is switched, as a function of the carbon dioxide and water content in the passenger compartment 3, by means of the air distribution device 19 into the sorption mode M1. In the sorption mode M1, as mentioned above, carbon dioxide and water are sorbed from the raw air RO of the passenger compartment 3 by the corresponding sorption unit 6, 7.

In a step S2, the other of the two sorption units 6, 7, for example, the second sorption unit 7, is switched by means of the air distribution device 19 into the desorption mode M2 in which, from the corresponding sorption unit 6, 7, carbon dioxide and water are desorbed into the supplied non-loaded regeneration air R1 and discharged into the environment U.

In a step S3, the steps S1 and S2 are performed alternately such that always one of the two sorption units 6, 7 is operated in the sorption mode M1 while the other one of the two sorption units 6, 7 is operated in the desorption mode M2.

Figure 20:
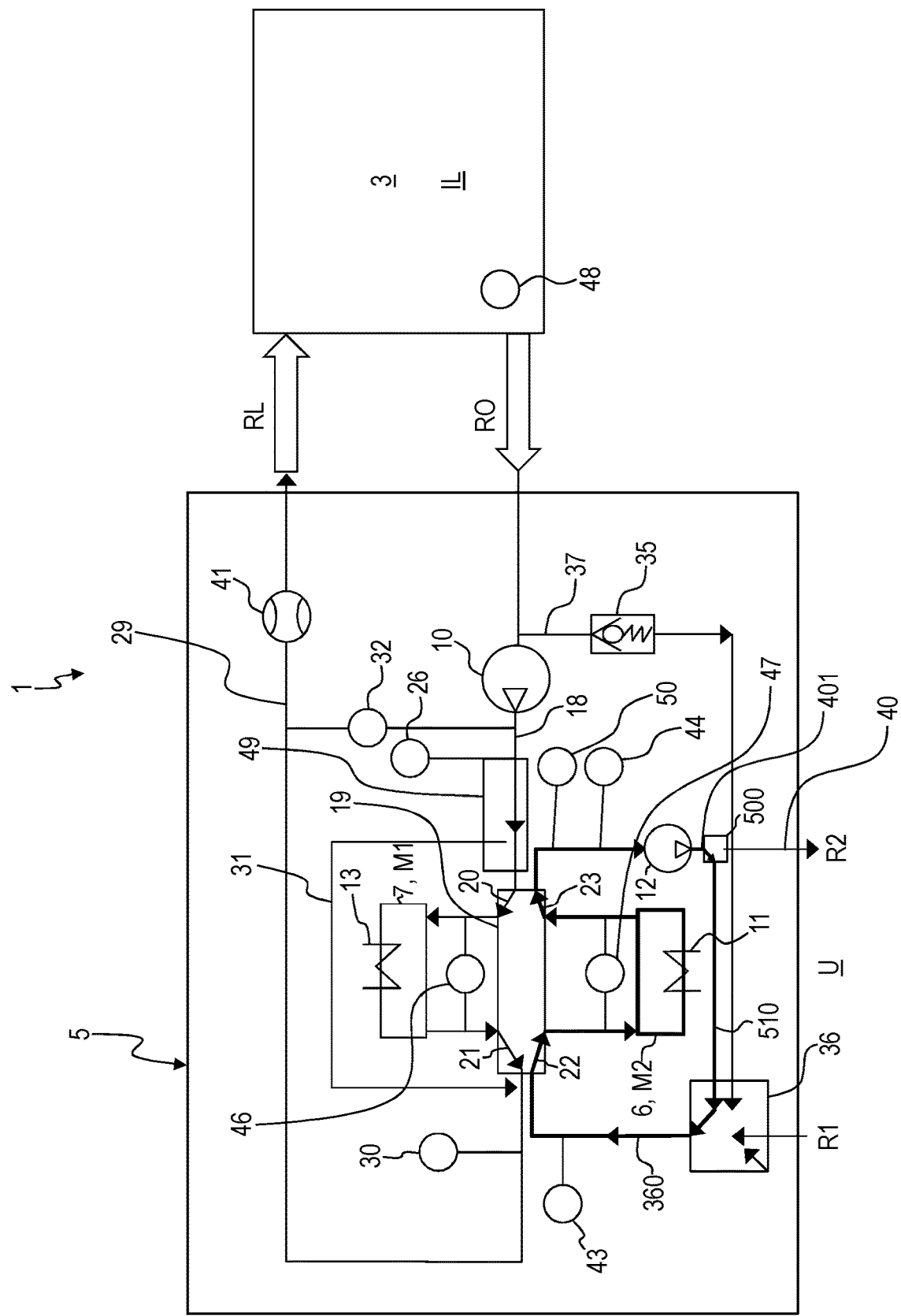
FIG. 20 shows a further embodiment of the motor vehicle according to FIG. 5 with a recirculation conduit in the desorption circuit.
Figure 21:
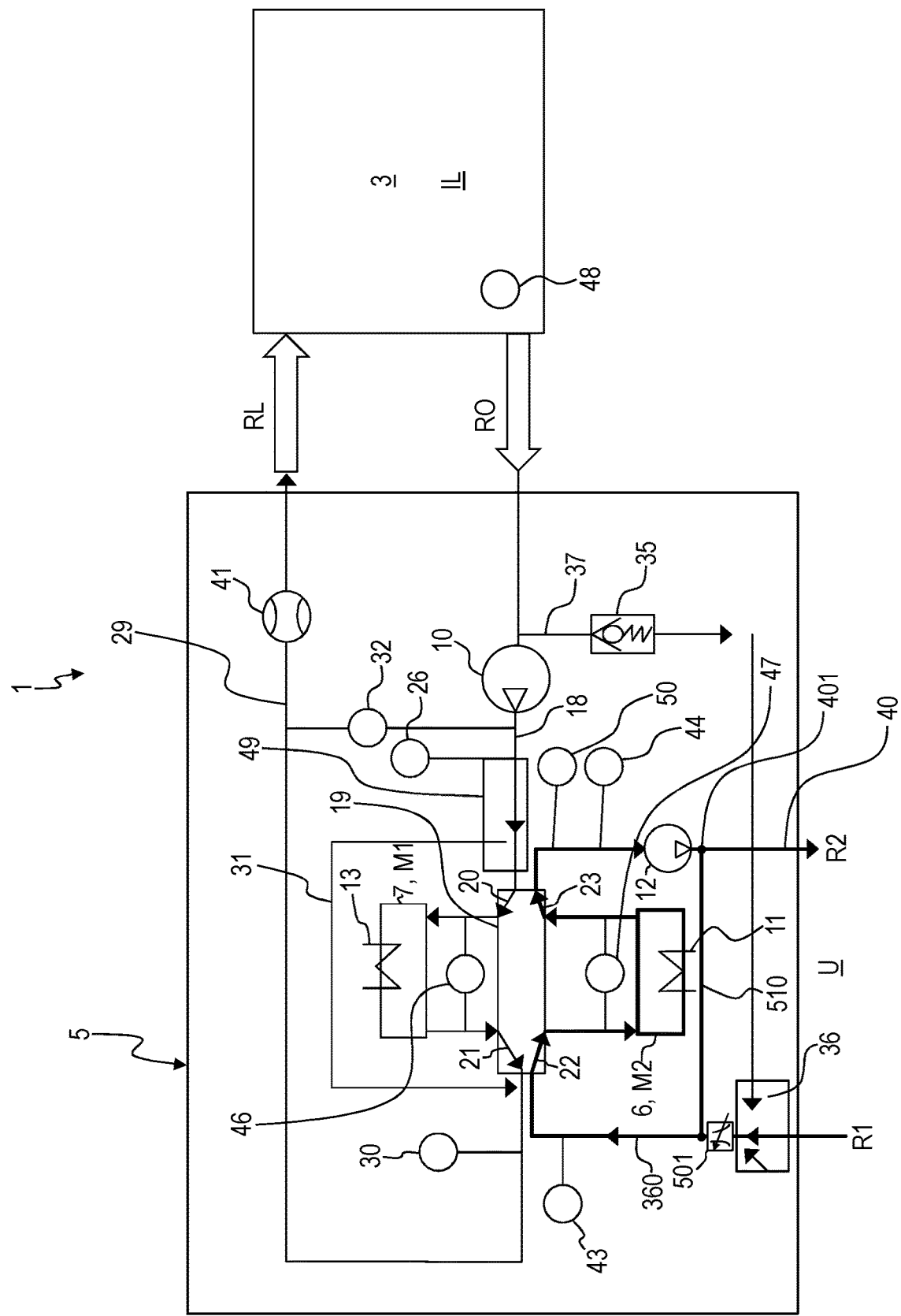
FIG. 21 shows a further embodiment of the motor vehicle according to FIG. 5 with a throttled recirculation conduit in the desorption circuit.
Figure 22:
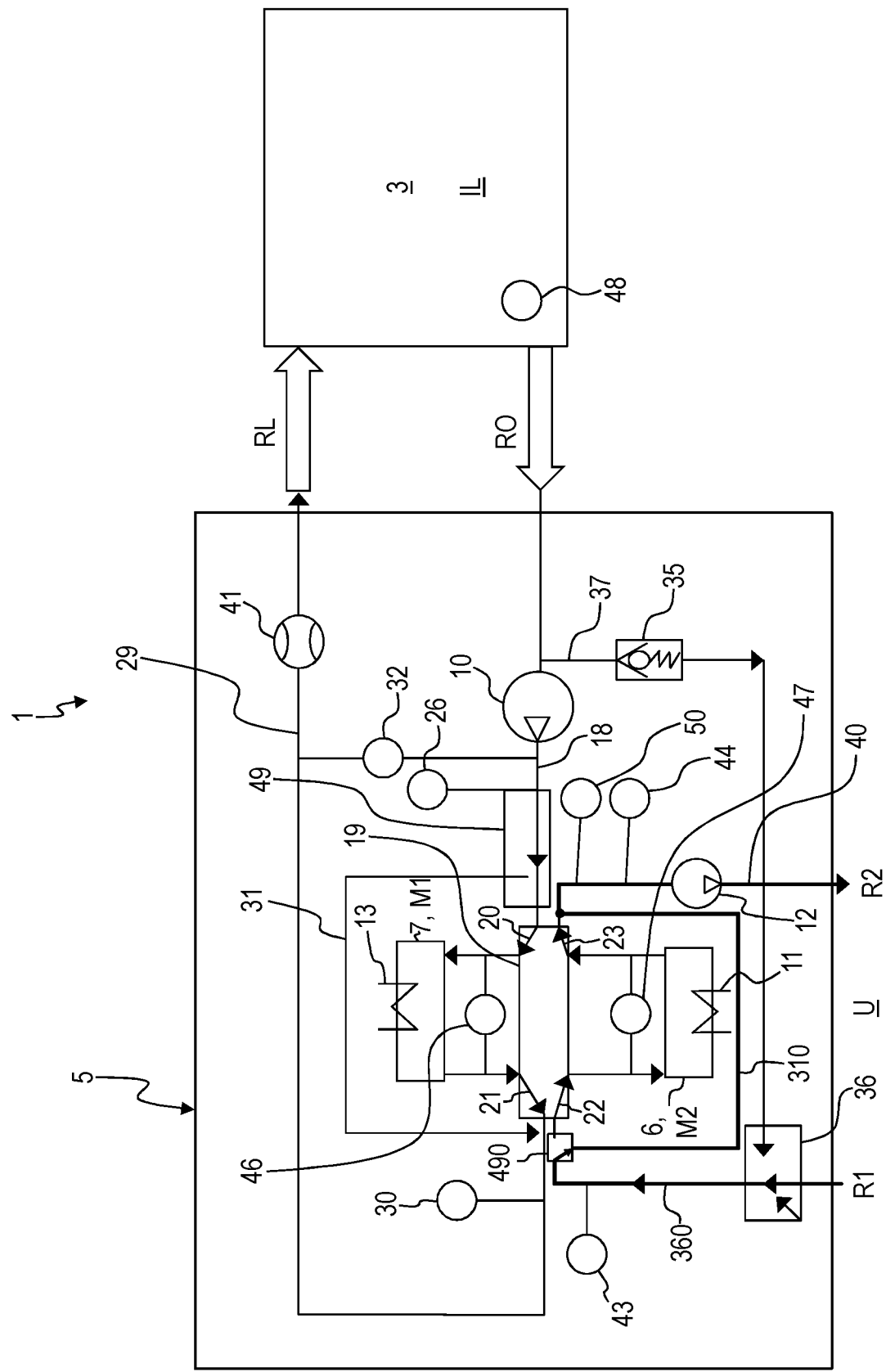
FIG. 22 a further embodiment of the motor vehicle according to FIG. 5 with a bypass conduit in the desorption circuit.

In the hydraulic circuit diagrams of the motor vehicle 1 with device 5 for combined reduction of the carbon dioxide and water content in an enclosed air volume of FIG. 20, FIG. 21, and FIG. 22, which represent each further embodiments of FIG. 5, the desorption blower device 12 is active again. The fluid paths which are illustrated in bold are the active ones for the selected switch positions.

According to FIG. 20, the sorption unit 6 is in the desorption mode M2 and is flowed through by a regeneration air volume flow R1. Downstream at the pressure side of the desorption blower device 12, a branch 401 is provided in the desorption conduit 40 which can be switched by means of the recirculation valve 500. The branch 401 opens into a recirculation conduit 510 that is connected in fluid communication with an inlet of the regeneration valve 36, wherein, by means of the regeneration valve 36, a fourth switch position can be switched in which the regeneration air R1 from the recirculation conduit 510 can be supplied to the sorption unit 6 which is in the desorption mode, and vice versa, so that by means of the desorption blower device 12 the regeneration air R1 can be selectively recirculated through the sorption units 6, 7 or can be guided into the environment.

This has advantages with respect to energy consumption because the heat quantity introduced once for regeneration is used optimally for desorption and heat losses are reduced thereby.

An alternative embodiment according to which also an at least partial recirculation of the at least partially loaded recirculation air R2, i.e., of the air volume flow which has passed at least once the sorption unit 6 which is in the desorption mode, is illustrated in FIG. 21.

Accordingly, a throttle valve 501, in particular an adjustable throttle valve 501, is arranged in fluid communication between the outlet of the regeneration valve and the inlet of the recirculation conduit into the regeneration air conduit, by means of which the proportion of freshly supplied non-loaded regeneration air R1 can be adjusted. According to this embodiment, at the branch 401 no recirculation valve 500 is provided but the branch is embodied as a non-switched branch (e.g., distributor, T member, Y member or the like). This has the advantage that the desorption of the sorption unit which is in the desorption mode can always be realized at a sufficient concentration differential, which aids in reducing the total regeneration duration.

In FIG. 22, a further embodiment is illustrated that comprises a second bypass conduit 310 as well as a second bypass valve 490. The second bypass valve 490 comprises two switch states between which it can be switched selectively. According to the first switch state, regeneration air R1 can be supplied to the sorption unit 6, 7 which is in the desorption mode M2. According to the second switch state, regeneration air R1 can be guided by means of the bypass conduit 310 by bypassing the sorption units 6, 7 into the environment U. This concerns primarily a test or calibration mode useable for testing sensors that are optionally provided in the system. Or in the meaning of an "emergency mode" when the pressure loss across one of the sorption units surpasses a predetermined limit value.

Figure 23:
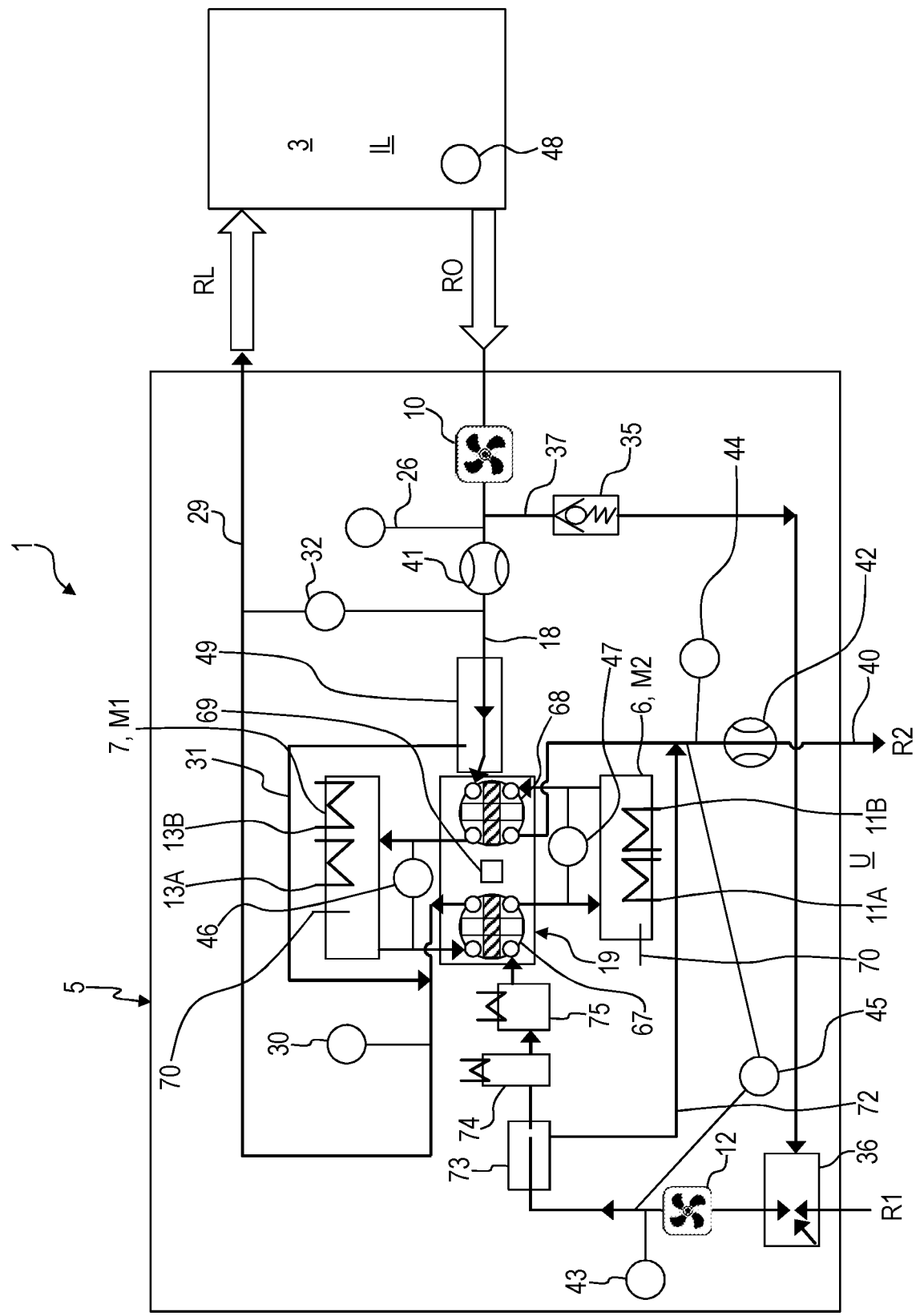
FIG. 23 shows a greatly simplified schematic view of a further embodiment of a motor vehicle.
Figure 24:
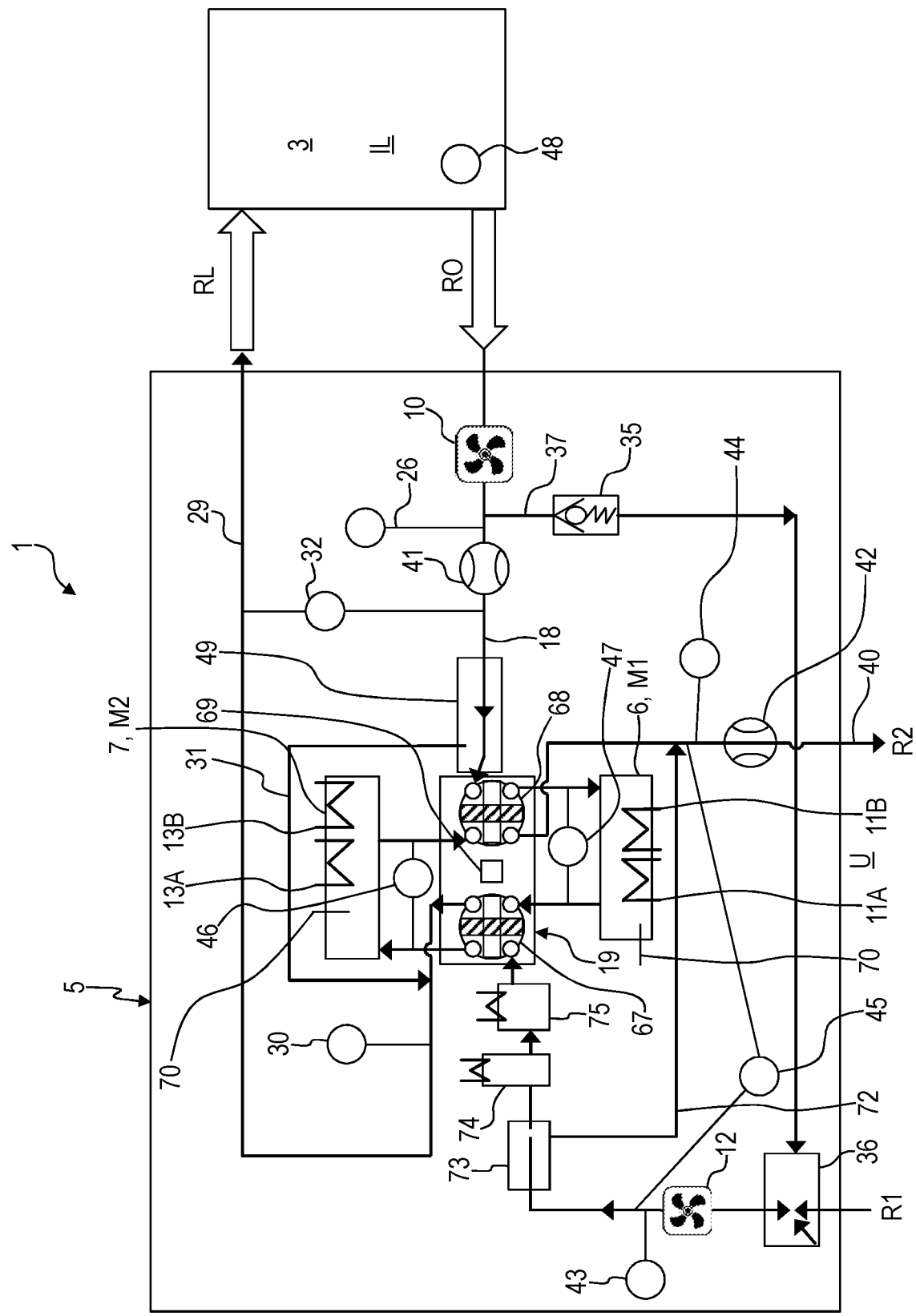
FIG. 24 shows a further greatly simplified schematic view of the motor vehicle according to FIG. 23.

FIGS. 23 and 24 show the motor vehicle 1 in a further embodiment of the device 5. In this embodiment of the motor vehicle 1, the device 5 also operates independent of the air conditioning device 4. In operation of the motor vehicle 1, the interior air IL is loaded in the passenger compartment 3 with $CO_2$ and $H_2O$. The loaded interior air IL is the aforementioned raw air RO. The raw air RO loaded with $CO_2$ and $H_2O$ can be at least partially supplied to the device 5 and thus to the sorption units 6, 7. In particular, the raw air RO is supplied to a first blower device 10. The first blower device 10 is mounted in this context at the pressure side. The first blower device 10 can however also be mounted at the suction side.

Downstream of the first blower unit 10, a conduit 18 is provided which supplies the raw air RO to an air distribution device 19. The air distribution device 19 comprises a plurality of flap units 67, 68. Correspondingly, the air distribution device 19 can also be referred to as flap device or flap system. The flap units 67, 68 can be controlled by a common flap actuator 69. A first flap unit 67 can be brought selectively into fluid communication with the first sorption unit 6 or with the second sorption unit 7. Accordingly, a second flap unit 68 can also be moved selectively into fluid communication with the first sorption unit 6 or with the second sorption unit 7.

The conduit 18 is in fluid communication with the air distribution device 19 which, in turn, is in fluid communication with the two sorption units 6, 7. Depending on the switch position of the flap units 67, 68, the raw air RO can be supplied selectively either to the first sorption unit 6 or to the second sorption unit 7. In or at the conduit 18, a sensor 26, in particular a $CO_2$, $H_2O$ and/or temperature sensor, can be provided.

A conduit 29 connects the air distribution device 19 with the passenger compartment 3. The conduit 29 can also comprise a sensor 30, in particular a $CO_2$, $H_2O$ and/or temperature sensor. By means of the sensor 30, for example, it can be detected when the sorption unit 6, 7 which is in the sorption mode M1 is exhausted. Between the conduits 18, 29, a bypass conduit 31, in particular an adsorber bypass conduit, is provided for bypassing the sorption units 6, 7. Moreover, between the conduits 18, 29, a sensor 32, in particular a pressure sensor, is also provided which can detect a pressure difference between the conduits 18, 29.

The device 5 comprises a regeneration valve 36. The regeneration valve 36 is preferably a three-way valve. The ambient air UL is supplied as non-loaded regeneration air R1 to the regeneration valve 36. Moreover, the interior air IL as non-loaded regeneration air R1 can also be supplied via a conduit 37 to the regeneration valve 36. In or at the conduit 37, a check valve 35 is provided.

Via a conduit 40, loaded regeneration air R2 can be discharged to the environment U. The conduit 40 comprises a volume flow sensor 42. The volume flow sensor 42 can be referred to as desorption volume flow sensor. Downstream of the regeneration valve 36, a second blower device 12 is provided. In this context, the second blower device 12 is positioned at the pressure side, i.e., upstream of the sorption unit 6, 7. The second blower device 12 can also be provided at the suction side, i.e., downstream of the sorption units 6, 7. The second blower device 12 discharges the loaded regeneration air R2 into the environment U.

A volume flow sensor 41 can be arranged downstream of the first blower device 10. A volume flow sensor 42 is provided downstream of the air distribution device 19 in the conduit 40. Downstream of the second blower device 12, a further sensor 43, in particular a $CO_2$, $H_2O$ and/or temperature sensor, is provided. Moreover, a further sensor 44, in particular a CO2, H2O and/or temperature sensor, is provided in or at the conduit 40. Moreover, a sensor 45 is provided that is suitable to detect a pressure difference between the conduit 40 and the air distribution device 19. The sensor 45 is provided downstream of the sensor 43.

Each sorption unit 6, 7 has associated therewith a sensor 46, 47, in particular a differential pressure sensor. A sensor 48, in particular as $CO_2$, $H_2O$ and/or temperature sensor, can also be provided in the passenger compartment 3. In order to activate or deactivate the bypass conduit 31, a bypass valve 49 is provided. Each sorption unit 6, 7 comprises a plurality of temperature sensors 70, 71. For example, each sorption unit 6, 7 has correlated there with four such temperature sensors 70, 71. Each sorption unit 6, 7 can comprise a plurality of heating elements 11A, 11B, 13A, 13B. The heating elements 11A, 11B, 13A, 13B are optional. The heating elements 11A, 11B, respectively, 13A, 13B can be arranged in a sandwich-type arrangement. The device 5 comprises a further conduit 72, in particular a regeneration bypass conduit. The conduit 72 opens upstream of the volume flow sensor 42 into the conduit 40. By means of the conduit 72, the air distribution device 19 can be bypassed. The conduit 72 extends from a bypass valve 73 that is arranged downstream of the air distribution device 19 to the conduit 40.

Downstream of the bypass valve 73, i.e., between the bypass valve 73 and the air distribution device 19, an optional heating element 74, in particular a heat exchanger, is provided. By means of the heating element 74, for example, waste heat of an electric motor, of an internal combustion engine, or of a battery cooling system can be transmitted to the non-loaded regeneration air R1. Downstream of the heating element 74, an optional further heating element 75 is provided. The heating element 75 is arranged between the heating element 74 and the air distribution device 19. The heating element 75 is also suitable for transmitting heat to the non-loaded regeneration air R1. The heating element 75 can be, for example, an electrical heating element.

FIG. 23 shows a switch position of the air distribution device 19 in which the first sorption unit 6 is in the desorption mode M2 and in which the second sorption unit 7 is in the sorption mode M1. The second flap unit 68 is switched such that the raw air RO is supplied by means of the first blower device 10 to the second sorption unit 7. The first flap unit 67 is switched such that the raw air RO from which $H_2O$ and $CO_2$ have been removed is now supplied as clean air IL to the passenger compartment 3 via the conduit 29.

As has been mentioned before, the first sorption unit 6 is in the desorption mode M2. For this purpose, by means of the regeneration valve 36 and the second blower device 12 non-loaded regeneration air R1 is taken in from the environment U. The non-loaded regeneration air R1 is then supplied to the heating element 74 that is embodied preferably as a heat exchanger and preheated. At the same time, the regeneration air R1 can be further heated by means of the optional heating element 75 that is arranged downstream of the heating element 74. By means of the first flap unit 67 of the air distribution device 19, the heated regeneration air R1 is supplied to the first sorption unit 6. Optionally, the first sorption unit 6 itself can also comprise heating elements 11A, 11B which are activated in the desorption mode M2. However, this is not mandatorily required. The second flap unit 68 is switched such that the loaded regeneration air R2 is discharged via the conduit 40 into the environment U.

FIG. 24 shows a switch position of the air distribution device 19 in which the first sorption unit 6 is in the sorption mode M1 and in which the second sorption unit 7 is in the desorption mode M2. For this purpose, the flap units 67, 68 of the air distribution device 19 are switched correspondingly. The heating element 74 and the heating element 75 are used in order to heat the non-loaded regeneration air R1 supplied to the second sorption unit 7. The heating element 74 and the heating element 75 can thus be used for the desorption mode M2 of both sorption units 6, 7.

Since the heating element 74 and/or the heating element 75 are not integrated into the sorption units 6, 7 but in flow direction are arranged upstream thereof, namely, before inflow into the air distribution device 19, the heat introduction into the sorption units 6, 7 introduced by the air flow can be realized more homogeneously than in an in-situ heating via the electrical heating elements 11A, 11B, 13A, 13B in the sorption units 6, 7. Upon heating via the air flow, the heat transmission is realized mainly by convection, while upon heating by means of the heating elements a higher heat conduction proportion is present. By use of the external heating elements 74, 75, the desorption is realized faster. Moreover, the completion of the desorption mode M2 can be detected more easily with regard to measuring technology wherein the final criterion for the completion of the desorption is that the input temperature is identical to the output temperature. A further advantage is that only one heating element 74 or only one heating element 75 is required that can heat both sorption units 6, 7.

EMPLOYED REFERENCE CHARACTERS 1 motor vehicle
2 car body
3 enclosed air volume/passenger compartment
4 air conditioning device
5 device
6 sorption unit
7 sorption unit
8 sorbent
9 sorbent
10 blower device
11 heating element
11A heating element
11B heating element
12 blower device
13 heating element
13A heating elements
13B heating element
14 conduit
15 conduit
16 conduit
17 conduit
18 conduit
19 air distribution device
20 valve
21 valve
22 valve
23 valve
24 conduit
25 conduit
26 sensor
27 conduit
28 conduit
29 conduit
30 sensor
31 bypass conduit
310 second bypass conduit
32 sensor
33 conduit
34 conduit
35 check valve
36 regeneration valve
360 regeneration air conduit
37 conduit
38 conduit
39 conduit
40 (desorption) conduit
401 branch of desorption conduit
41 volume flow sensor
42 volume flow sensor
43 sensor
44 sensor
45 sensor
46 sensor
48 sensor
49 bypass valve
490 second bypass valve
50 pressure sensor
500 recirculation valve
501 throttle valve, adjustable
510 recirculation conduit
51 blower device
52 valve 53 cooling element
54 heating element
55 drive element
56 blower wheel
57 blower wheel
58 arrow
59 coupling
60 coupling
61 gear wheel
62 gear wheel
63 cross shaft
64 cross shaft
65 coupling element
66 coupling element
67 flap unit
68 flap unit
69 flap actuator
70 temperature sensor
71 temperature sensor
72 conduit
73 bypass valve
74 heating element
75 heating element
IL interior air
M1 sorption mode
M2 desorption mode
RL clean air
RO raw air
R1 non-loaded regeneration air
R2 loaded regeneration air
S1 step
S2 step
S3 step
U environment
UL ambient air
Q heat

What is claimed is:

1. A device for combined reduction of a carbon dioxide and water content in an enclosed air volume, the device comprising:
a first sorption unit configured to sorb carbon dioxide and water;
a second sorption unit configured to sorb carbon dioxide and water,
wherein the first sorption unit and the second sorption unit each comprise a plurality of sorbents, and
wherein the first sorption unit and the second sorption unit each are configured to:
be transferred from a sorption mode into a desorption mode and from the desorption mode into the sorption mode;
in the sorption mode, sorb carbon dioxide and water from a raw air of the enclosed air volume; and
in the desorption mode, desorb carbon dioxide and water to a supplied regeneration air;
an air distribution device configured to switch the first sorption unit and the second sorption unit, as a function of the carbon dioxide and water content in the enclosed air volume, alternately from the sorption mode into the desorption mode and from the desorption mode into the sorption mode such that, in at least one operating state of the device, one of the first sorption unit and the second sorption unit is in the sorption mode while another one of the first sorption unit and the second sorption unit is in the desorption mode;
a regeneration valve comprising a first switch position and a second switch position,
wherein, in the first switch position, the first sorption unit or the second sorption unit in the desorption mode is supplied with the supplied regeneration air that is removed from an environment of the enclosed air volume, and
wherein, in the second switch position, the first sorption unit or the second sorption unit in the desorption mode is supplied with the supplied regeneration air that is removed from the enclosed air volume;
a desorption blower device configured to supply the supplied regeneration air to the first sorption unit or the second sorption unit in the desorption mode; and
a desorption conduit arranged downstream at a pressure side of the desorption blower device, the desorption conduit comprising a branch that opens into a recirculation conduit,
wherein the regeneration valve further comprises an inlet and an outlet,
wherein the device further comprises a regeneration air conduit connected to the outlet of the regeneration valve,
wherein the recirculation conduit is connected in fluid communication to the inlet of the regeneration valve, or the recirculation conduit is connected in fluid communication to the regeneration air conduit downstream of the outlet of the regeneration valve,
wherein the recirculation conduit is connected in fluid communication to the regeneration valve,
wherein the regeneration valve further comprises a fourth switch position, and
wherein, in the fourth switch position, the first sorption unit or the second sorption unit in the desorption mode is supplied with the supplied regeneration air from the recirculation conduit.

2. The device according to claim 1, wherein, in the desorption mode, the supplied regeneration air guided through the first sorption unit or the second sorption unit in the desorption mode is supplied as loaded regeneration air into the environment of the enclosed air volume.

3. The device according to claim 1, wherein the air distribution device comprises a plurality of valves configured to be switched such that, in operation of the device, the first sorption unit or the second sorption unit in the sorption mode is supplied with the raw air from the enclosed air volume to remove the carbon dioxide and the water from the raw air, and the first sorption unit or the second sorption unit in the desorption mode is supplied with the supplied regeneration air to remove the carbon dioxide and the water from the first sorption unit or the second sorption unit in the desorption mode.

4. The device according to claim 1, further comprising one or more heating elements associated with the first sorption unit and the second sorption unit and configured to introduce heat into the first sorption unit or the second sorption unit in the desorption mode.

5. The device according to claim 4, wherein each of the one or more heating elements is integrated in a respective one of the first sorption unit and the second sorption unit.

6. The device according to claim 4, wherein the one or more heating elements are positioned upstream of the first sorption unit and the second sorption unit.

7. The device according to claim 1, wherein the first sorption unit and the second sorption unit comprise a common heating element configured to introduce heat into the first sorption unit or the second sorption unit in the desorption mode.

8. The device according to claim 1, wherein the regeneration valve further comprises a third switch position, and
wherein, in the third switch position, the first sorption unit or the second sorption unit in the desorption mode is regenerated under vacuum.

9. The device according to claim 1, further comprising a recirculation valve configured to switch the branch so that the supplied regeneration air is selectively recirculated through the first sorption unit and the second sorption unit or the supplied regeneration air is guided into the environment of the enclosed air volume via the desorption conduit.

10. The device according to claim 1, further comprising a throttle valve arranged in fluid communication between the outlet of the regeneration valve and a location where the recirculation conduit is connected to the regeneration air conduit.

11. The device according to claim 1, further comprising a blower device configured to supply the raw air to the first sorption unit or the second sorption unit in the sorption mode.

12. The device according to claim 11, wherein the blower device is part of an air conditioning device.

13. The device according to claim 1, further comprising:
a bypass conduit; and
a bypass valve configured to be selectively switched from a first switch state into a second switch state and from the second switch state into the first switch state,
wherein, in the first switch state, the raw air is supplied to the first sorption unit or the second sorption unit in the sorption mode, and
wherein, in the second switch state, the raw air is guided via the bypass conduit around the first sorption unit and the second sorption unit back into the enclosed air volume.

14. The device according to claim 1, further comprising:
a bypass conduit; and
a bypass valve configured to be selectively switched from a first switch state into a second switch state and from the second switch state into the first switch state,
wherein, in the first switch state, the supplied regeneration air is supplied to the first sorption unit or the second sorption unit in the desorption mode, and
wherein, in the second switch state, the supplied regeneration air is supplied via the bypass conduit by bypassing the first sorption unit and the second sorption unit into the environment of the enclosed air volume.

15. The device according to claim 1, wherein the first sorption unit and the second sorption unit are configured to remove any one or any combination of fine particles, nitrogen oxides and volatile organic compounds from the raw air.

16. The device according to claim 15, wherein the plurality of sorbents comprise:
a first sorbent configured to adsorb carbon dioxide;
a second sorbent configured to adsorb water; and
third sorbents configured to remove any one or any combination of fine particles, nitrogen oxides and volatile organic compounds from the raw air.

17. The device according to claim 16, wherein the third sorbents are arranged between two carrier layers, or the first sorbent, the second sorbent, and the third sorbents are mixed with each other.

18. The device according to claim 1, wherein the first sorption unit and the second sorption unit are configured to remove any one or any combination of allergens, bacteria and viruses from the raw air.

19. A motor vehicle comprising the device according to claim 1, wherein the device is configured to be controlled, based on an occupation state of the enclosed air volume with passengers, to maintain the carbon dioxide and water content in the enclosed air volume in a predetermined tolerance field.

20. A device for combined reduction of a carbon dioxide and water content in an enclosed air volume, the device comprising:
a first sorption unit configured to sorb carbon dioxide and water;
a second sorption unit configured to sorb carbon dioxide and water,
wherein the first sorption unit and the second sorption unit each comprise a plurality of sorbents, and
wherein the first sorption unit and the second sorption unit each are configured to:
be transferred from a sorption mode into a desorption mode and from the desorption mode into the sorption mode;
in the sorption mode, sorb carbon dioxide and water from a raw air of the enclosed air volume; and
in the desorption mode, desorb carbon dioxide and water to a supplied regeneration air;
an air distribution device configured to switch the first sorption unit and the second sorption unit, as a function of the carbon dioxide and water content in the enclosed air volume, alternately from the sorption mode into the desorption mode and from the desorption mode into the sorption mode such that, in at least one operating state of the device, one of the first and second sorption units is in the sorption mode while another one of the first and second sorption units is in the desorption mode;
a bypass conduit; and
a bypass valve configured to be selectively switched from a first switch state into a second switch state and from the second switch state into the first switch state,
wherein, in the first switch state, the supplied regeneration air is supplied to the first sorption unit or the second sorption unit in the desorption mode, and
wherein, in the second switch state, the supplied regeneration air is supplied via the bypass conduit by bypassing the first sorption unit and the second sorption unit into an environment of the enclosed air volume.

21. A method for operating a device for combined reduction of a carbon dioxide and water content in an enclosed air volume, the device comprising a first sorption unit configured to sorb carbon dioxide and water, and a second sorption unit configured to sorb carbon dioxide and water, the method comprising:
a) controlling an air distribution device to switch one of the first sorption unit and the second sorption unit, as a function of the carbon dioxide and water content in the enclosed air volume, into a sorption mode to sorb carbon dioxide and water from a raw air of the enclosed air volume;
b) controlling the air distribution device to switch another one of the first sorption unit and the second sorption unit into a desorption mode to desorb carbon dioxide and water to a supplied regeneration air;
c) alternately performing steps a) and b) such that, in at least one operating state, one of the first sorption unit and second sorption unit is in the sorption mode while another one of the first sorption unit and the second sorption unit is in the desorption mode;
d) controlling a regeneration valve to be in a first switch position in which the first sorption unit or the second sorption unit in the desorption mode is supplied with the supplied regeneration air that is removed from an environment of the enclosed air volume;

e) controlling the regeneration valve to be in a second switch position in which the first sorption unit or the second sorption unit in the desorption mode is supplied with the supplied regeneration air that is removed from the enclosed air volume; and f) controlling the regeneration valve to be in a third switch position in which the first sorption unit or the second sorption unit in the desorption mode is regenerated under vacuum.

22. The method according to claim 21, further comprising introducing heat into the first sorption unit or the second sorption unit in the desorption mode.

23. The method according to claim 21, further comprising:

measuring in the enclosed air volume the carbon dioxide and water content; and controlling, based on the measured carbon dioxide and water content, the device such that the carbon dioxide and water content in the enclosed air volume is maintained within a predetermined tolerance field.

24. The method according to claim 23, further comprising:

detecting an occupation state of the enclosed air volume with passengers; and controlling, based on the detected occupation state of the enclosed air volume with passengers, the device such that the carbon dioxide and water content in the enclosed air volume is maintained within the predetermined tolerance field.

\* \* \* \* \*